United States Patent [19]

Shoyab et al.

[11] Patent Number: 5,428,012

[45] Date of Patent: * Jun. 27, 1995

[54] ONCOSTATIN M AND NOVEL COMPOSITIONS HAVING ANTI-NEOPLASTIC ACTIVITY

[75] Inventors: Mohammed Shoyab; Joyce M. Zarling, both of Seattle; Hans Marquardt, Mercer Island; Marcia B. Hanson, Seattle; Thomas J. Brown, Poulsbo, all of Wash.

[73] Assignee: Oncogen Limited Partnership, Seattle, Wash.

[*] Notice: The portion of the term of this patent subsequent to Jun. 9, 2009 has been disclaimed.

[21] Appl. No.: 85,279

[22] Filed: Jul. 1, 1993

Related U.S. Application Data

[60] Continuation of Ser. No. 428,195, Oct. 27, 1989, abandoned, which is a division of Ser. No. 144,574, Jan. 15, 1988, abandoned, which is a continuation-in-part of Ser. No. 115,139, Oct. 30, 1987, abandoned, and a continuation-in-part of Ser. No. 46,846, May 4, 1987, Pat. No. 5,120,535, which is a continuation-in-part of Ser. No. 935,283, Nov. 26, 1986, abandoned, which is a continuation-in-part of Ser. No. 811,235, Dec. 20, 1985, abandoned.

[51] Int. Cl.$^6$ .................. C12P 21/02; A61K 37/02; C12N 15/00
[52] U.S. Cl. .................. 514/12; 424/85.5; 424/85.1; 514/21; 530/350
[58] Field of Search .............. 530/350; 424/85.5, 85.1; 514/12, 21

[56] References Cited

U.S. PATENT DOCUMENTS

| | | | |
|---|---|---|---|
| 4,582,800 | 4/1986 | Crowl | 435/701 |
| 4,708,948 | 11/1989 | Iuata et al. | 514/2 |
| 4,711,845 | 12/1987 | Gelfand et al. | |
| 4,737,580 | 11/1987 | Twardzik et al. | |
| 4,743,679 | 5/1988 | Cohen et al. | |
| 4,952,507 | 8/1990 | Woodward | |
| 5,120,535 | 6/1992 | Marquardt et al. | 424/85.5 |

FOREIGN PATENT DOCUMENTS 0199016  1/1986  European Pat. Off.

OTHER PUBLICATIONS

Zarling et al. "Oncostatin M: A Growth Regulator . . . . lymphoma cells", PNAS 83: pp. 9739-9743 (1986).
Brown et al., "Purification and Characterization of Cystostatic Lymphokines Produced by Activated Human T Lymphocytes," *J. Immunol.* 139:2977-2983 (1987).
Seyedin et al., *J. Biol. Chem.* 262:1946(1987).
Seyeden et al., "Purification and Characterization Two Cartilage-Inducing Factors from Bovine Demineralized Bone," *PNAS. USA* 82:2267-2271 (1985).
Holley et al., *PNAS USA* 77(10):5989-5992 (1980).
Ellingsworth et al., *Journal of Biological Chemistry* 261(26):12362-12367, (1986).

(List continued on next page.)

*Primary Examiner*—Howard E. Schain
*Attorney, Agent, or Firm*—Pennie & Edmonds

[57] ABSTRACT

Novel compositions comprising Oncostatin M and congeners thereof, as well as methods for their preparation and methods for their use are provided. The compositions may be prepared by isolation from natural sources, or by recombinant means in either prokaryotic or eukaryotic host cells. In addition, the DNA and polypeptide sequences for Oncostatin M are disclosed. The compositions find use in modulating growth of cells, in particular inhibition of tumor cell proliferation, and stimulation of normal cell growth, especially cells involved in hematopoiesis. Cell growth inhibition compositions may additionally include an adjunctive agent comprising at least one of a transforming growth factor, tumor necrosis factor, or an interferon. Receptors having high affinity for Oncostatin M may additionally be used to screen polypeptides for Oncostatin M-like activity. Methods for use of antibodies to the compositions and probes specific for Oncostatin M mRNA as a means for detecting tumor cells are also provided.

4 Claims, 6 Drawing Sheets

OTHER PUBLICATIONS

Moses et al., "Type-β Transforming Growth Factor is a Growth Factor is a Growth Stimulator and a Growth Inhibitor," *Cancer Cells 3/Growth Factors and Transformation*, pp. 65–71 (1985).

Holley et al., *Cell Biology Reports* 7:525–526 (1983).

Holley et al., *Cell Biology International Reports* 7(7):141–147 (1983).

Cheifetz et al., *Cell* 48:409–414 (1987).

Ikeda et al., *Biochemistry* 26:2406–2410 (1987).

Massague, Joan, *Cell* 49:437–438 (1987).

Hanks et al., *PNAS USA* 85:79–82 (1988).

Lathe, *J. Mol. Biol.* 183:1–12.

Suggs, *PNAS USA* 78:6613–6617 (1981).

Docherty et al., *Nature* 318:66–69 (1985).

Dixon et al., *Nature* 321:75–79 (1986).

Anderson et al., *PNAS USA* 80:6838–6842 (1983).

Jaye et al., *Nucl. Acids Res.* 11:2325–2335 (1983).

Ullrich et al., *EMBO J.* 3:361–364 (1984).

Ullrich et al., *Nature* 309:418–425 (1984).

Derynck et al., *Nature* 316:701–705 (1985).

Derynck et al., *Cell* 38:287–297 (1984).

Gorski et al., *Cell* 43:461–465 (1985).

Marcus, *Chem. Abstracts* 103:54444M (1985).

Maniatis et al., *Molecular Cloning—A Laboratory Manual*, Cold Spring Harbor Laboratories, pp. 226–227, 408–413, 422–423, 433, 507–520 (1982).

Ikuta et al., "Human lymphocyte Fc receptor for IgE: Sequence homology of its cloned cDNA with animal lectins," *PNAS USA* 84:819–823 (1987).

Gunderson et al., *J. of Cellular Biochemistry*, Supp. 12A, p. 224 (1988).

Oncogen, NL 86 03,209 (1987) C.A. 110:6095w.

Cate et al., *Cell* 45:685–698 (1986).

Itakura et al., "Chemical DNA Synthesis and Recombinant DNA Studies," *Science* 209:1401–1405 (1980).

Tavernier et al., *Molecular Cloning and Analysis of Lymphokines*, Ed. Webb et al., Academic Press, Inc. 13:194–195 (1987).

Linsley et al., "Identification and Characteriation of Cellular Receptors for the Growth Regulator, Oncostatin M," *J. Biol. Chem.* 264:4282–4289 (1989).

Iwata et al., *Cancer Res.* 45:2689–2694 (1985).

Morinage et al., *J. Immunol.* 143:3538–3542 (1989).

Aggarwal et al., "Human Lymphoterin," *J. Biol. Chem.* 259:686–691 (1984).

Aggarwal et al., "Primary structure of human lymphotorin derived from 1788 lymphobkstoid cell line," *J. Biol. Chem.* 260(4):2334–2344 (1985).

Sporn et al., "Autocrine Secretion and Malignant Transformation of Cells," *NEJM*, pp. 878–880 (1980).

Burgess, "Medical Aspects of Growth Factors," *Ciba Foundation Symposium 116*, p. 261 (1985).

Lee et al., *J. of Immunology* 133(3):1083–1086 (1984).

Amento et al., *PNAS* 79:5307–5311 (1982).

Zabeau et al., "Enhanced expression of cro-β-galactosidase fusion proteins under the control of the $P_R$ promoter of bacteriophage λ", i EMBO J. 1(10):1217–1224 (1982).

Miyake et al., "Secretion of human interferon-α induced by secretion vectors containing a promoter and signal sequence of alkaline phosphatase gene of *Escherichia coli*," *3-Biochem. Genetics Abstracts* 103(3):17753r (1985).

Chang et al., "Alkaline phosphatase-mediated processing and secretion of recombinant proteins, DNA sequences for use therein and cells transformed using such sequences," *3-Biochem. Genetics Abstracts* 106(17):133062a (1987).

Byeon et al., "Post-transcriptional Regulation of Chloramphenicol Acetyl Transferase," *J. Bacteriology* 158(2):543–550.

European Search Report dated 28 Dec. 1988.

```
-384  GCATCTACTCGGCCCTCATTCTGCAGCACGATGAGGTGACAGTCACGGAGGATAAGATCAATGCCCTCATTAAAGCAGCCGGTGTA  -298

AATGTTGAGCCTTTTTGCCTGGCTTGTTTTGCAAAGGCCCTGGCCAACGTCAACATTGGGAGCCTCATCTGCAATGTAGGGGCCGGTGGACCTGCTCCA  -199

GCAGCTGGTGCTGCACCAGCAGGAGTCCTGCCCCCCTCCACTGCTGCCTCCAGCTGAGGAGAAGAAAGTTGGAAGCAAAGAAGAAGAATCCGAGGAG  -100

TCTGATGATGACATGGGCTTTGGTCTTTTTGACTAAACCTCTTTTATAACATGTTCAATAAAAAGCTGAACTGCACTCCTGTTTCCAAGCATGGCGAGC  -1

10                              20
Met Ala Ala Ile Gly Ser Cys Ser Lys Glu Tyr Arg Val Leu Leu Gly Gln Leu Gln Lys Gln Thr Asp Leu Met
ATG GCG GCT ATA GGC AGC TGC TCG AAA GAG TAC CGC GTG CTC CTT GGC CAG CTC CAG AAG CAG ACA GAT CTC ATG  75

35                              45
Gln Asp Thr Ser Arg Leu Leu Asp Pro Tyr Ile Arg Ile Asp Thr Leu Arg Gly Leu Gly Asp Val Pro Lys Leu Arg Glu His Cys
CAG GAC ACC AGC AGG CTC CTG GAC CCC TAT ATA CGT ATC CAA GGC CTG GAT GTT CCT AAA CTG AGA GAG CAC TGC  150

60                              70
Arg Glu Arg Pro Gly Ala Phe Pro Ser Glu Glu Thr Leu Arg Gly Arg Arg Gly Phe Leu Gln Thr Leu
AGG GAG CGC CCC GGG GCC TTC CCC AGT GAG GAG ACC CTG AGG GGC CGG AGG GGC TTC CTG CAG ACC CTC  225

*                                   85                              95
Asn Ala Thr Leu Gly Cys Val Leu His Arg Leu Ala Asp Leu Glu Gln Arg Leu Pro Lys Ala Gln Asp Leu Glu
AAT GCC ACA CTG GGC TGC GTC CTG CAC AGA CTG GCC GAC TTA GAG CAG CGC CTC CCC AAG GCC CAG GAT TTG GAG  300

110                             120
Arg Ser Gly Leu Asn Ile Glu Glu Asp Leu Gly Lys Leu Gln Met Ala Arg Pro Asn Ile Gly Leu Arg Asn Asn
AGG TCT GGG CTG AAC ATC GAG GAC TTG GGG AAG CTG CAG ATG GCG AGG CCG AAC ATC CTC GGG CTC AGG AAC AAC  375
```

FIG. 3A

```
                                   135
Ile Tyr Cys Met Ala Gln Leu Leu Asp Asn Ser Asp Thr Ala Glu Pro Thr Lys Ala Gly Arg Gly Ala Ser Gln
ATC TAC TGC ATG GCC CAG CAG CTG CTG GAC AAC TCA GAC ACG GCT GAG CCC ACG AAG GCT GGC CGG GGG GCC TCT CAG    450

160                                                  145
Pro Pro Thr Pro Ala Ser Asp Phe Gln Arg Lys Leu Glu Gly Cys Arg Phe Leu His Gly Tyr His
CCG CCC ACC CCC GCC TCG GAT GCT TTT CAG CGC AAG CTG GAG GGC TGC AGG TTC CTG CAT GGC TAC CAT            525

185                 *         195
Arg Phe Met His Ser Val Gly Arg Val Phe Ser Lys Trp Gly Glu Ser Pro Asn Arg Ser Arg Arg His Ser Pro
CGC TTC ATG CAC TCA GTG GGG CGG GTC TTC AGC AAG TGG GGG GAG AGC CCG AAC CGG AGC CGG AGA CAC AGC CCC    600

220
His Gln Ala Leu Arg Lys Gly Val Arg Thr Arg Arg Pro Ser Arg Lys Gly Lys Arg Leu Met Thr Arg Gly Gln
CAC CAG GCC CTG AGG AAG GGT GTG CGC AGG ACC CGC AGG CCC TCC AGG AAA GGC AAG AGA CTC ATG ACC AGG GGA CAG   675

228
Leu Pro Arg ***
CTG CCC CGG TAG CCTCGAGAGCACCCCTTGCCGGTGAAGGATGCGGCAGGTGCTCTGTGGATGAGGAACCATCGAGGATGACAGCTCCCGGG         770

TCCCCAAACCTGTTCCCCTCTGTACTAGCCACTGAGAAGTGCACTTTAAGAGGTGGGAGCTGGGCAGACCCCTCTACCTCCTCCAGGCTGTGGGAGACAG    869

AGTCAGGCTGTTGCGCTCCACCTCAGCCCCAAGTTCCCCAGGCCCAGTGGGGTGGGCGGGCCACGCGGGACCGACTTTCCATTGATTCAGGGGT          968

CTGATGACACAGCTGACTCATGGCCGGGCTGACTGCCCCCTGCCTGCTCCCCGAGGCCTGCCGGTCCTTCCCTCTCATGACTGATTGCAGGGCCGTTGC   1067
```

FIG.3B

```
CCCCAGAGACTTCCTCCTCTTCCGTGTTTCTGAAGGGAGGAGGTCACAGCCTGAGCTGGCCTCCTCATCATGTCCCAAACCAGACACCTGGATGTCTG  1166

GGTGACCTCACTTTAGGCAGCCTGTAACAGCGGCAGGGTGTCCCAGGAGCCCTGATCCGGGGGTCCAGGGAATGGAGCTCAGGTCCCAGGCCAGCCCGA  1265

AGTCGCCACGTGGCCTGGGCAGGTCACTTTACCTCTGTGGACCTGTTTCTCTCTTGTGAAGCTAGGAGTTAGAGGCTGTACAAGGCCCCACTGCCT  1364

GTCGGTTGCTTGGATCCCTGACGTAAGGTGGATATTAAAAATCTGTAAATCAGGACAGGTGCTGCAAATGGCGCTGGGAGGTGTACACGGAGGTCTCT  1463

GTAAAAGCAGACCCACTCCCAGCGCCGGGAAGCCGTCTTGGGTCCTCGCTGCTGCTCCCCCTGGTGGTGGATCCTGGAATTTCTCACGCAGG  1562

AGCCATTGCTCTCCTAGAGGGGGTCTCAGAAACTGCGAGGCCAGTTCCTTGGAGGGACATGACTAATTTATCGATTTTTATCAATTTTTATCAGTTTTA  1661

TATTTATAAGCCTTATTTATGATGTATATTTAATGTTAATATTGTGCAAACTTATATATTTAAAACTTGCCTGGTTTCTAAA  1741
```

FIG.3C

ONCOSTATIN M AND NOVEL COMPOSITIONS HAVING ANTI-NEOPLASTIC ACTIVITY

CROSS-REFERENCED RELATED APPLICATIONS

This application is a continuation of U.S. application Ser. No. 07/428,195, filed Oct. 27, 1989 now abandoned, which is a divisional of Ser. No. 07/144,574, filed Jan. 15, 1988, now abandoned, which is a continuation-in-part of Ser. No. 07/115,139, filed Oct. 30, 1987, now abandoned and a continuation-in-part of Ser. No. 07/046,846, filed May 4, 1987, now U.S. Pat. No. 5,120,535, the latter being a continuation-in-part of Ser. No. 06/935,283, filed Nov. 26, 1986, now abandoned, which is a continuation-in-part of Ser. No. 06/811,235, filed Dec. 20, 1985, now abandoned, each of which applications is incorporated herein in its entirety.

INTRODUCTION

1. Technical Field

Cell growth regulatory compositions are disclosed, where the compounds work independently and provide for synergistic effects in combination.

2. Background

The ability to control tumor cell growth without serious side effects to the host organism has long been a goal in the continuing search for improved methods for treating cancer. Drugs or naturally occurring compounds usually have a broad range of activities towards different cells. Moreover, at concentrations which may be effective in inhibiting the growth of neoplastic cells, these compounds frequently demonstrate undesired effects on normal cells. Of particular interest therefore are compounds which selectively inhibit the growth of neoplastic cells while not inhibiting the growth of surrounding or other normal tissue.

Examples of such compounds are peptides such as the interferons and lymphocyte-derived tumor necrosis factor-$\beta$ (TNF-$\beta$) as well as TNF-$\alpha$, derived from myelocytic cells, which display cytostatic and/or cytocidal activity against transformed cell lines, but do not affect normal cells. However, even with those compounds such as the interferons which show inhibitory activity primarily towards tumor cells, not all tumor cells respond to the compound. In addition, reliable methods have not been developed to identify tumors which have a high probability of responding to a given compound. Furthermore, there may be a fine line between a therapeutic dose of a given compound and that which is physiologically unacceptable or toxic. There has also been reported synergy between low levels of different types of IFN or of IFN and other growth inhibiting peptides, such as lymphocyte-derived TNF-$\beta$.

There is therefore an interest in being able to identify those tumor cells which may respond to a given antiproliferative compound, and in being able to develop compositions which may be employed at low concentration when administered therapeutically, while still providing the desired growth inhibitory effects, and with minimal deleterious effects on normal cells.

Relevant Literature

Beal et al., *Cancer Biochem. Biophys.* (1979) 3:93–96 report the presence of peptides in human urine which inhibit growth and DNA synthesis more in transformed cells than in normal cells. Holley et al., *Proc. Natl. Acad. Sci.* (1980) 77:5989–5992 describe the purification of epithelial cell growth inhibitors. Letansky, *Biosci. Rep.* (1982) 2:39–45 report that peptides purified from bovine placenta inhibit tumor growth and thymidine incorporation in DNA to a greater extent in neoplasms than in normal cells. Chen, *Trends Biochem. Sci.* (1982) 7:364–365 reports the isolation of a peptide from ascites fluid with a cancer suppressing property. Redding and Schally, *Proc. Natl. Acad. Sci.* (1982) 79:7014–7018 report isolation of purified peptide(s) from porcine hypothalmi which exhibit antimitogenic activity against several normal and tumor cell lines. Sone et al., *Gann* (1984) 75:920–928 report the production of a factor(s) produced by human macrophages that inhibits the growth of certain tumor cells in vitro. Ransom et al., *Cancer Res.* (1985) 45:851–862, report the isolation of a factor called leukoregulin that inhibits replication of certain tumor cell lines and appears distinct from lymphotoxin, interferon and interleukin 1 and 2. Most of these factors have not been fully characterized, nor are their primary structures known.

Aggarwal et al., *J. Biol. Chem.* (1984) 259: 686–691 purified and characterized human lymphotoxin (LT) produced by a lymphoblastoid cell line and subsequently sequenced LT (Aggarwal et al., *J. Biol. Chem.* (1985) 260:2334). Gamma interferon ($\gamma$-IF) which is produced by lymphoid cells and has immunomodulatory and tumor inhibitory activity has been cloned and expressed. (Gray et al., *Nature* (1982) 295:503:508.) Tumor necrosis factor (TNF), which inhibits growth of some tumors and is produced by macrophages and certain leukemia cell lines has been characterized and the TNF cDNA was cloned and expressed in *E. coli* (Pennica et al., *Nature* (1984) 312:724).

A review of the family of compounds under the designation TGF-$\beta$ is provided by Sporn et al., *Science* (1986) 233:532–534. The structure and functional relationship with CIF-B (cartilage-inducing factor B) to TGF-$\beta$ is demonstrated by Seydin et al., *J. Biol. Chem.* (1987) 262:1946–1949. See also Seydin et al., *Proc. Natl. Acad. Sci. USA* (1985) 82:2267–2271.

Procedures for purification of growth inhibitor compounds have been described by Henderson et al., *J. Immunol.* (1983) 131:810–815 and Marquardt and Todaro, *J. Biol. Chem.* (1982) 257:5220–5225.

Synergy between low levels of different types of IFN or IFN and other growth inhibiting peptides like tumor necrosis factor-$\beta$ are described by Lee et al., *J. Immunol.* (1984) 133:1083–1086. The effects of TNF-$\beta$ and TNF-$\alpha$ are described by Sugarman et al., *Science* (1985) 230:943–945. Oncostatin M, its purification and characterization, are described by Zarling et al., *Proc. Natl. Acad. Sci. USA* (1986) 83:9739–9743.

Purification of Oncostatin M and synergy with other growth factors is described in Brown et al., *J. Immunol.* (1987) 139:2977–2983.

SUMMARY OF THE INVENTION

Novel compositions, as well as methods of preparation and use are provided, where the compositions are Oncostatin M, fragments or analogs thereof, or combinations of at least two agents, where one of the agents is Oncostatin M. Methods for isolation of Oncostatin M include purification from natural sources, as well as by cloning and expression in both prokaryotic and eukaryotic systems. Methods of use include growth inhibition of tumor cells.

BRIEF DESCRIPTION OF THE DRAWINGS

FIG. 3 is the entire sequence of Oncostatin M cDNA clone OncM46; and

DESCRIPTION OF THE SPECIFIC EMBODIMENTS

Figure 1A:
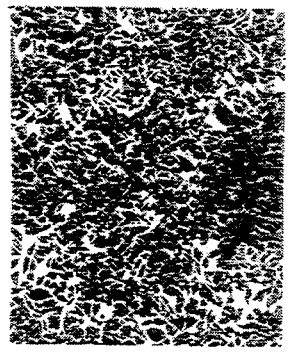
FIG. 1 is a series of photomicrographs of cells treated with Oncostatin M wherein (A–C) are A375 melanoma cells treated with 0, 5 and 100 GIA units, respectively, and (D–F) are WI38 fibroblasts treated with 0, 5 and 100 GIA units, respectively.
Figure 1B:
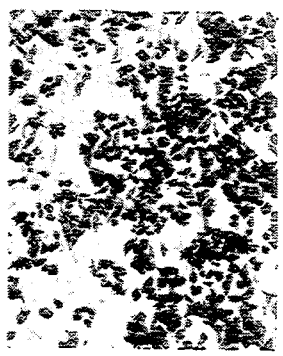
Figure 1C:
Figure 1D:
Figure 1E:
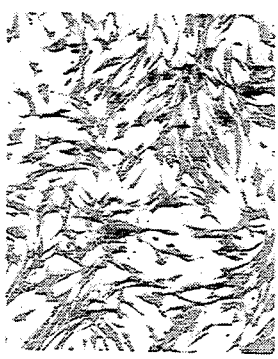
Figure 1F:
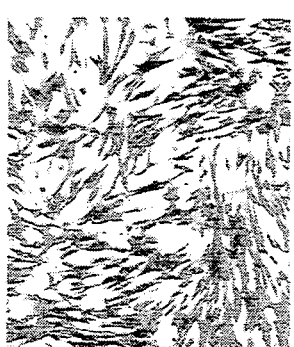

Novel anti-neoplastic compositions, and methods of use, are provided comprising Oncostatin M. In addition, compositions comprising Oncostatin M and at least one other component are also provided. Oncostatin M is characterized as being produced by activated leukocytes, for example from the acid soluble fraction of conditioned media of stimulated U937 cells or conditioned media of stimulated normal human peripheral blood lymphocytes (PBL).

Human Oncostatin M has the following amino acid sequence:

```
                         10                              20                             30
A—A—I—G—S—C—S—K—E—Y—R—V—L—L—G—Q—L—Q—K—Q—T—D—L—M—Q—D—T—S—R—L—
                         40                              50                             60
L—D—P—Y—I—R—I—Q—G—L—D—V—P—K—L—R—E—H—C—R—E—R—P—G—A—F—P—S—E—E—
                         70                              80                             90
T—L—R—G—L—G—R—R—G—F—L—Q—T—L—N—A—T—L—G—C—V—L—H—R—L—A—D—L—E—Q—
                        100                             110                            120
R—L—P—K—A—Q—D—L—E—R—S—G—L—N—I—E—D—L—E—K—L—Q—M—A—R—P—N—I—L—G—
                        130                             140                            150
L—R—N—N—I—Y—C—M—A—Q—L—L—D—N—S—D—T—A—E—P—T—K—A—G—R—G—A—S—Q—P—
                        160                             170                            180
P—T—P—T—P—A—S—D—A—F—Q—R—K—L—E—G—C—R—F—L—H—G—Y—H—R—F—M—H—S—V—
                        190                             200                            210
G—R—V—F—S—K—W—G—E—S—P—N—R—S—R—R—H—S—P—H—Q—A—L—R—K—G—V—R—R—T—
                        220                   227
R—P—S—R—K—G—K—R—L—M—T—R—G—Q—L—P—R
```

Oncostatin M is further characterized as having a molecular weight of about 17 to 19 kiloDaltons (kD), particularly about 18 kD, as determined by size exclusion chromatography, and as having an apparent molecular weight of approximately 28 kD as determined by polyacrylamide gel electrophoresis under reducing or non-reducing conditions. Active preparations of isolated Oncostatin M contain a mixture of high mannose and complex N-linked oligosaccharide. However, non-glycosylated preparations of Oncostatin M retain cell growth modulatory activity.

Oncostatin M is further characterized by its activity toward certain cell strains. The subject polypeptide lacks cytotoxic activity against WI26 and WI38 human fibroblasts, and mouse L929 cells which are sensitive to tumor necrosis factor, and a γ-interferon-sensitive human tumor cell line. It does not inhibit proliferation of normal human T-lymphocytes and does not inhibit granulocytic/myelocytic colony formation from bone marrow cells at concentrations up to 100 GIA units/ml.

Further, Oncostatin M stimulates proliferation of normal human fibroblasts as exemplified by WI38 and WI26 cells and inhibits proliferation of tumor cells such as A375, HBT10, A549 and SK-MEL28 and may augment growth of colony forming cells from normal bone marrow. Oncostatin M does not suppress human proliferative or cytotoxic T cell responses in mixed leukocyte culture reactions (MLC) at concentrations of 500 GIA units/ml.

The subject polypeptide is found to be stable to moderate acid and base and to heat treatment at 56° C.

Oncostatin M-like materials, including Oncostatin M fragments, mutants of the polypeptide, as well as fusion peptides comprising Oncostatin M or a functional portion thereof, having the biological activity of the intact Oncostatin M including cell growth modulation activity, receptor binding activity or immunologic activity are also provided.

The polypeptides of this invention include congeners of Oncostatin M, namely compounds having at least one biological activity corresponding to that of Oncostatin M and having at least one amino acid sequence having substantially the same amino acid sequence as Oncostatin M, where the congener may be of greater or lesser amino acid number than Oncostatin M. Biological activity includes immunological cross-reactivity with naturally occurring human Oncostatin M, or binding to an Oncostatin M receptor molecule with high affinity. By immunological cross-reactivity is meant that an antibody induced by a novel polypeptide of this invention will cross-react with intact Oncostatin M, at least when Oncostatin M is in a denatured state. By high affinity is meant a dissociation constant ($K_d$) of at least about $10^{-7}$ M. By Oncostatin M receptor is meant a binding site on the surface of a cell which specifically binds Oncostatin M with high affinity, the binding being saturable and not inhibited by structurally unrelated polypeptides. Some of the polypeptides may also retain the cell growth modulatory activity of naturally occurring Oncostatin M, which includes inhibition of growth of neoplastic cells and stimulation of growth of normal cells including cells of the hematopoietic system. The cell growth modulatory activity may be different from naturally occurring Oncostatin M, usually reduced.

The present invention also includes polypeptide fragments comprising an amino acid sequence having at least 8 amino acids, either consecutive or non-consecutive, that correspond to an amino acid sequence in the complete sequence depicted above. Also included are polypeptides having at least 8 amino acids that differ from the above sequence by no more than 3, usually no more than 1 amino acid. That difference can be either the insertion of an amino acid, the deletion of an amino acid or the substitution of one amino acid for another, particularly a conservative substitution. Usually the polypeptide will contain at least 10, more usually at least 12, consecutive amino acids that correspond to the sequence depicted above and differ by no more than one amino acid.

For purposes of the subject invention, the various amino acids can be divided into a number of subclasses. The following table indicates the subclasses:

| aliphatic neutral | | | | | |
|---|---|---|---|---|---|
| non-polar | G | A | P | V | L | I |
| polar | S | T | C | M | N | Q |
| acidic | D | E | | | | |
| basic | K | R | | | | |
| aromatic | F | H | Y | W | | |

By conservative substitution, it is meant that amino acids from the same subclass (i.e., either neutral aliphatic, acidic aliphatic, basic aliphatic or aromatic), more particularly the same polarity, will be substituted for each other. Desirably, amino acids of two to four carbon atoms or five to six carbon atoms will define monomer groupings in the aliphatic subclass.

Novel polypeptides of interest will for the most part have a formula comprising an N-terminal region, $N_R$, a middle region, $M_R$, and a C-terminal region, $C_R$. $N_R$ is characterized as having from 8 to 72 amino acids of which from 2 to 21 are charged amino acids with approximately a 4:3 ratio of basic to acid amino acids, 0 to 4 amino acids are aromatic and 0 to 3 prolines.

$M_R$ is a short linking group of from about 20 to 96 amino acids of which from about 5 to about 24 amino acids are charged amino acids, with approximately equal numbers of acidic and basic amino acids. In addition, the $M_R$ may include 0 to 2 aromatic amino acids and 0 to 7 prolines.

$C_R$ is characterized as having from 20 to 59 amino acids having 3 to 17 basic amino acids and 0 to 2 acidic amino acids, and from 3 to 7 aromatic amino acids. The C-terminal region may additionally include from 0 to 4 prolines.

The polypeptides will not exceed about 1000 amino acids in length. Usually they will have fewer than one hundred amino acids, more usually fewer than fifty amino acids. Thus, the polypeptides can be readily synthesized. Usually when polypeptides exceed 100 amino acids in length, those polypeptides may be polymers of fragments of Oncostatin M having fewer than 100 amino acids each, or fusion proteins where Oncostatin M or a fragment thereof is fused to a second peptide which can be an antigen, enzyme, enzyme fragments, N-terminal amino acids from a secreted expression product, etc. In addition, a radiolabel or a cytotoxic agent such as a toxin A-chain fragment or a trageting molecule such as a hormone or antibody can be coupled covalently to either the Oncostatin M-like polypeptide or the second peptide.

Particularly, the higher molecular weight polypeptides can be at least one polypeptide fragment of fewer than about 100 amino acids joined covalently to a large immunogenic polypeptide carrier to provide for immunogenicity. Exemplary of such protein carriers are bovine serum albumin, keyhole limpet hemocyanin (KLH) and the like. Those conjugated polypeptides will be useful for inducing antibodies in an appropriate host organism. The antibodies can be used to determine the presence and/or concentration of Oncostatin M in a bodily fluid, the presence of which may further be used as a means of detecting the presence of a tumor cell, to bind to Oncostatin M and thus modulate its activity, and to purify Oncostatin M, as by use in an affinity column.

Preparation of Oncostatin M and Other Subject Compounds

Oncostatin M may be obtained in a variety of ways. It is available from naturally occurring sources, particularly growth medium supplemented with an appropriate inducer such as an ingenol or phorbol and conditioned by a cell line (U937) derived from a human histiocytic lymphoma (Sundstrom and Nilsson, *Int. J. Cancer* (1976) 17:565–577) or a mitogen such as phytohemoglutinen (PHA) and conditioned by normal human peripheral blood lymphocytes (PBL).

U937 cells can be induced to differentiate into cells having characteristics of macrophages following treatment with a variety of agents (Harris et al., *Cancer Res.* (1985) 45:9–13). For production of Oncostatin M, the U937 cells may be grown in a conventional nutrient medium with serum and treated with an appropriate inducer, particularly 12-o-tetradecanoylphorbol-13-acetate (TPA). Usually, from about 5–20 ng/ml of the inducer may be employed. The initial number of cells is from about $10^5$ to $10^6$ cells/ml.

After treating cells with the inducer for a sufficient time, generally three to six days, the supernatant is removed, the cells washed with serum-free nutrient medium, attached cells washed again with serum-free medium and the cells incubated for at least 12 hours, usually not more than about 48 hours, in serum-free nutrient medium, e.g. RPMI-1640 medium. The supernatant is then collected and the cells removed by centrifugation. The cell-free supernatant was then tested for cell growth inhibitory activity (GIA) as described in the experimental plan. The supernatant contains about 50 to 500 units of GIA/ml (see Experimental for definition of GIA units.)

Oncostatin M can also be obtained from mitogen-stimulated normal human peripheral blood lymphocytes (PBLs). PBLs can be isolated from leukofractions by diluting the fractions and centrifuging them over Ficoll gradients. Cells collected from the gradient interface are washed and shock-lysed to remove red blood cells. Remaining cells are collected by centrifugation, resuspended in buffer containing serum and thrombin, agitated and the platelet aggregate allowed to settle for a short period of time. The suspended cells are transferred, recovered by centrifugation, resuspended in serum and transferred to a column containing nylon wool. The column is incubated to allow the attachments of monocytes and B-lymphocytes and then washed. Most peripheral blood T lymphocytes do not adhere and are eluted from the column. The non-adherent cells are cultured at 37° in culture medium, e.g. RPMI-1640 medium, and treated with an appropriate inducer, e.g. phytohemagglutinin (about 1 to 5 mg/l), for about 100 hours. The supernatants are collected, centrifuged to remove cells, and concentrated, for example by ultrafiltration or dialysis.

After isolating the cell-free supernatant from either U937 cells or normal PBLs, the conditioned medium is concentrated, conveniently using a hollow fiber system or an ultrafiltration membrane, followed by dilution with acetic acid (to a concentration of 0.1N acetic acid) followed by concentrating about ten-fold and the dilution and concentration repeated. The concentrate may be lyophilized and used directly or the lyophilized product can be used for further purification.

The subject Oncostatin M can be purified so as to be substantially free of cellular components employing various purification techniques. These techniques can include solvent extraction, gel permeation chromatography, reversed phase-HPLC, electrophoresis, or the like. For active fragments, various synthetic techniques may be employed, where the polypeptide will be synthesized on a solid support. A number of commercial synthesizers are available and may be used to advantage, for example, from SmithKline, Beckman, Applied Biosystems, etc.

Usually, the product is purified to provide a specific activity of at least about 10 GIA units/ng protein, more usually 100 GIA units/ng.

Oncostatin M and fragments or analogs thereof as well as fusion proteins in which Oncostatin M is fused to, for example, a leader sequence from a prokaryotic protein or a eukaryotic protein can also be prepared by employing recombinant DNA techniques. Further, the amino acid sequence can be used to design a probe and a cDNA or a genomic library from stimulated or unstimulated peripheral blood lymphocytes or histiocytic lymphoma (U937) cells screened for hybridizing sequences. To enhance the likelihood of identifying the correct sequence, a cDNA library from unstimulated cells or other cell lines which do not produce Oncostatin M may be used to cross-hybridize. Those sequences from the stimulated cells which do not hybridize will be concentrated as to the desired sequence. Sequences which hybridize to the probe and do not cross-hybridize with cDNA from cells which do not produce Oncostatin M may be screened by using *Xenopus oocytes*. An assay for the expression of Oncostatin M using restriction fragments inserted into a prokaryotic expression vector such as λgt-11 then screening with antibodies for Oncostatin M to detect a cross-reactive peptide fragment or the like can be used.

Once a complete gene has been identified, either as cDNA or chromosomal DNA, it may then be manipulated in a variety of ways to provide for expression. Both prokaryotic and eukaryotic hosts may be employed, which may include bacteria, yeast, insect cells, and mammalian cells, e.g. *E. coli*, COS cells, CHO cells, monkey kidney cells, and silkworm cells (sf9). Therefore, where the gene is to be expressed in a host which recognizes the wild-type transcriptional and translational regulatory regions of Oncostatin M, the entire gene with its wild-type 5'- and 3'-regulatory regions may be introduced into an appropriate expression vector. Various expression vectors exist employing replication systems from mammalian viruses, such as Simian Virus 40, adenovirus, bovine papilloma virus, vaccinia virus, insect baculovirus, etc. These replication systems have been developed to provide for markers which allow for selection of transfectants, as well as providing for convenient restriction sites into which the gene may be inserted.

Where the gene is to be expressed in a host which does not recognize the naturally occurring wild-type transcriptional and translational regulatory regions, further manipulation will be required. Conveniently, a variety of 3'-transcriptional regulatory regions are known and may be inserted downstream from the stop codons. The non-coding 5'-region upstream from the structural gene may be removed by endonuclease restriction, Bal31 resection, or the like. Alternatively, where a convenient restriction site is present near the 5'-terminus of the structural gene, the structural gene may be restricted and an adaptor employed for linking the structural gene to the promoter region, where the adaptor provides for the lost nucleotides of the structural gene.

Various strategies may be employed for providing for an expression cassette, which in the 5'-3'-direction of transcription has a transcriptional regulatory region and a translational initiation region, which may also include regulatory sequences allowing for the induction of regulation; the structural gene under the transcriptional and translational control of the initiation region; and translational and transcriptional termination regions. The expression cassette may additionally include at least one of leader sequences from bacteriophage or bacterial genes which provide for stability of the expression product, and secretory leader sequences which provide for secretion of the expression product, as well as marker genes.

Choice of appropriate regulatory sequences will take into account the following factors which affect expression. In terms of transcriptional regulation, the amount and stability of messenger RNA are important factors which influence the expression of gene products. The amount of mRNA is determined by the copy number of the particular gene, the relative efficiency of its promoter and the factors which regulate the promoter, such as enhancers or repressors. The stability of the mRNA is governed by the susceptibility of the mRNA to ribonuclease enzymes. In general, exonuclease digestion is inhibited by the presence of structural motifs at the ends of the mRNA; palindromic structures, altered nucleotides, or specific nucelotide sequences. Endonuclease digestion is believed to occur at specific recognition sites within the mRNA and stable mRNAs would lack these sites. There is also some evidence that mRNAs undergoing high levels of translation are also protected from degradation by the presence of ribosomes on the mRNA.

In terms of translational regulation, given the presence of mRNA, expression can be regulated by influencing the rate of initiation (ribosome binding to the mRNA), the rate of elongation (translocation of the ribosome across the mRNA), the rate of post-translational modifications and the stability of the gene product. The rate of elongation is probably affected by codon usage, in that the use of codons for rare tRNAs may reduce the translation rate. Initiation is believed to occur in the region just upstream of the beginning of the coding sequence. In prokaryotes, in most cases this region contains a consensus nucleotide sequence of AGGA, termed the Shine-Dalgarno sequence. While this sequence characterizes the ribosomal binding site, it is evident that sequences both upstream and downstream can influence successful initiation. In eukaryotes, translational enhancer sequences have been detected which regulate expression.

Evidence also points to the presence of nucleotide sequences within the coding region which can affect ribosome binding, possibly by the formation of structural motifs through which the ribosome recognizes the initiation site. Position of the AGGA sequence with respect to the initiating ATG codon can influence expression. It is thus the interaction of all of these factors which determines a particular expression rate. Highly expressed genes have evolved a combination of all of these factors to yield a particular rate of expression. Design of an expression system to yield high levels of gene product must take into consideration not only the particular regions that have been determined to influence expression but also how these regions (and thus their sequences) influence each other.

Illustrative transcriptional regulatory regions or promoters include, for bacteria, the β-gal promoter, lambda left and right promoters, trp and lac promoters, trp-lac fusion promoter, etc.; for yeast, glycolytic enzyme promoters, such as ADH-I and -II promoters, GPK promoter, and PGI promoter, TRP promoter, etc.; for mammalian cells, SV40 early and late promoters, adenovirus major late promoters, etc.

The transcriptional regulatory region may additionally include regulatory sequences which allow expression of the structural gene to be modulated, e.g. by presence or absence of nutrients or expression products in the growth medium, temperature, etc. For example, in prokaryotic cells expression of the structural gene may be regulated by temperature using a regulatory sequence comprising the bacteriophage lambda $P_L$ promoter together with the bacteriophage lambda $O_L$ operator and the CI857 temperature-sensitive repressor. Regulation of the promoter is achieved through interaction between the repressor and the operator.

In eukaryotic cells, regulatory sequences can include, e.g., the cytomegalovirus enhancer sequence which can be fused to a promoter sequence such as the SV40 promoter, forming a chimeric promoter, or inserted elsewhere in the expression cassette, preferably in close proximity to the promoter sequence. Expression of the structural gene also can be amplified by, e.g, ligating in tandem a gene for a dominant amplifiable genetic marker 5' or 3' to the structural gene and growing the host cells under selective conditions. An example of an amplifiable gene is the gene for dihydrofolate reductase (dhfr), expression of which may be increased in cells rendered resistant to methotrexate (mtx), a folate antagonist.

Of particular interest are expression cassettes capable of expressing Oncostatin M which employ the lac operator-promoter, the tac promoter, or the lambda $P_L$ promoter-$O_L$ operator, and a temperature-sensitive repressor, particularly in conjunction with the λ-Cro, lac or N-gene ribosome binding site. The structural gene is joined downstream from the ribosome binding site, so as to be under the regulatory control of the transcriptional regulatory region and the translational regulatory region.

Stability of the expression product may be achieved by providing for synthesis of a fused protein comprising N-terminal amino acids from, for example, a bacteriophage lambda N-gene or Cro gene, or a bacterial alkaline phosphatase gene. The leader sequence is provided upstream from and in reading frame with the structural gene. The leader sequences of interest include from about 8 to about 35, preferably from about 15 to about 25 N-terminal amino acids from a prokaryotic gene, for example a bacteriophage lambda N-gene or Cro gene, or a bacterial alkaline phosphatase gene.

In addition, a fused gene may be prepared by providing a 5'-sequence to the structural gene which encodes a secretory leader and processing signal. Illustrative secretory leaders include the secretory leaders of penicillinase, α-factor, immunoglobulins, T-cell receptors, outer membrane proteins, serum albumin, insulin, digestive tract enzymes, β-transforming growth factor and the like. By fusion in proper reading frame of the secretory leader with the structural gene, the mature Oncostatin M or congener may be secreted into the medium.

At least one additional amino acid may be inserted between the structural gene and the leader sequence, the intervening amino acid(s) providing for, for example, and enzymatic or chemical cleavage site for cleavage of the fusion protein. Alternatively, the fusion protein comprising the leader sequence and the structural gene product may find use without cleavage of the mature polypeptide.

The expression cassette may be included within a replication system for episomal maintenance in an appropriate cellular host or may be provided without a replication system, where it may become integrated into the host genome. The DNA may be introduced into the host in accordance with known techniques, such as transformation, using calcium phosphate-precipitated DNA, electroporation, transfection by contacting the cells with the virus, microinjection of the DNA into cells or the like.

Once the structural gene has been introduced into the appropriate host, the host may be grown to express the structural gene. The host cell may be grown to high density in an appropriate medium. Where the promoter is inducible, such as in a prokaryotic system, permissive conditions will then be employed, for example, temperature change, exhaustion, or excess of a metabolic product or nutrient, or the like. In a mammalian system, where an amplifiable gene is used in tandem with the structural gene, the appropriate means for amplification will be employed.

Where secretion is provided for, the expression product, either fused or unfused, may be isolated from the growth medium by conventional means. Where secretion is not provided for, the host cells may be harvested and lysed in accordance with conventional conditions. The desired product is then isolated and purified in accordance with known techniques, such as chromatography, electrophoresis, solvent extraction, or the like.

The recombinant products may be glycosylated or non-glycosylated, having the wild-type or other glycosylation. In general, the glycosylation will differ by not more than about 50% usually by not more than about 20% from the wild-type glycosylation. The amount of glycosylation will depend in part upon the sequence of the particular peptide, as well as the organism in which it is produced. Thus expression of the product in *E. coli* cells will result in an unglycosylated product, and expression of the product in insect cells generally will result in less glycosylation than expression of the product in mammalian cells.

Uses of Oncostatin M and Other Subject Compounds

The subject compounds can be used in a wide variety of ways, both in vivo and in vitro. The subject compounds can be used for making antibodies to the subject compounds, which may find use in vivo or in vitro. The antibodies can be prepared in conventional ways, either by using the subject polypeptide as an immunogen and injecting the polypeptide into a mammalian host, e.g. mouse, cow, goat, sheep, rabbit, etc., particularly with an adjuvant, e.g. complete Freunds adjuvant, aluminum hydroxide gel, or the like. The host may then be bled and the blood employed for isolation of polyclonal antibodies, or in the case of the mouse, the peripheral blood lmphocytes or splenic lymphocytes (B-cells) employed for fusion with an appropriate myeloma cell to immortalize the chromosomes for monoclonal expression of antibodies specific for the subject compounds.

Either polyclonal or monoclonal antibodies may be prepared, which may then be used for diagnosis or detection of the presence of the subject polypeptide in a sample, such as cells or a physiological fluid, e.g., blood. Detection of the subject polypeptide in a bodily fluid may also be used as an indication of the presence of a tumor cell. The antibodies may also be used in affinity chromatography for purifying the subject polypeptide and isolating it from natural or synthetic sources. The antibodies may also find use in controlling the amount of the subject polypeptide associated with cells in culture or in vivo, whereby growth of the cells may be modified.

Probes comprising sequences complementary to Oncostatin M mRNA may also be prepared and used as a diagnostic aid, for example, the presence and/or amount of Oncostatin M mRNA in a cell may be used for detecting the presence of a tumor cell. A test sample comprising a cell, tissue sample or bodily fluid believed to contain hybridizing sequences can be treated so as to lyse any cells, then treated with a denaturing agent such as guanidine hydrochloride to release single-stranded mRNA. The probe labeled with, for example, $^{32}P$ or biotinylated nucleotides, can then be hybridized to the cellular mRNA to form a double-stranded complex which may be detected by means of the label. For some purposes it may be desirable to quantitate the amount of Oncostatin M MRNA. This may be done by comparing the amount of label detected in reference samples containing known amounts of single-stranded Oncostatin M mRNA with the amount of label detected in the test sample.

The subject compound may be used as a ligand for detecting the presence of receptors for the subject compound. In this way, cells may be distinguished in accordance with the presence of and the density of receptors for the subject compound, monitoring the effect of various compounds on the presence of such receptors as well as determining the sensitivity of a given cell to the effects of the subject compound. Additionally, peptides believed to have Oncostatin M-like biological activity may be evaluated by comparing their ability to bind to the Oncostatin M receptor with that of naturally occurring Oncostatin M. Generally, the test peptides can be evaluated by incubating the test peptide together with labeled Oncostatin M or another peptide which binds with high affinity to the Oncostatin M receptor with a preparation containing Oncostatin M receptors, and observing the amount of inhibition of binding of the labeled Oncostatin M, as described in the Experimental section. Evaluation of whether test peptides which bind to the receptor are Oncostatin M agonists or antagonists can then be determined by observing their effect on a biological function associated with Oncostatin M, for example, inhibition of growth of tumor cells, as described in the Experimental section.

The subject compound may be used in in vitro cultures to inhibit the growth of cells or cell lines sensitive to the subject polypeptide as distinguished from cells which are not sensitive. Thus, heterogeneous cell mixtures or cell lines can be freed of undesirable cells, where the undesirable cells are sensitive to the subject polypeptide.

The subject compositions may be used in the treatment of a wide variety of neoplastic conditions, such as carcinomas, sarcomas, melanomas, lymphomas, leukemias, which may affect a wide variety of organs, such as the blood, lungs, mammary organ, prostate, intestine, liver, heart, skin, pancrease, brain, etc.

The subject polypeptide may be administered in vivo in the case of neoplastic conditions, for example, by injection, intralesionally, peritoneally, subcutaneously, or the like. The subject compound may be used in vitro to eliminate malignant cells from marrow for autologous marrow transplants or to inhibit proliferation or eliminate malignant cells in other tissue, e.g. blood, prior to reinfusion.

The subject compositions may also be used as a treatment in disorders of the hematopoietic system, especially as a means of stimulating hematopoiesis in patients with suppressed bone marrow function, for example, patients suffering from aplastic anemia, inherited or acquired immune deficiency, or patients undergoing radiotherapy or chemotherapy.

The compositions of the present invention may be used for treating a wide variety of wounds including substantially all cutaneous wounds, corneal wounds, and injuries to the epithelial-lined hollow organs of the body. Wounds suitable for treatment include those resulting from trauma such as burns, abrasions, cuts, and the like as well as from surgical procedures such as surgical incisions and skin grafting. Other conditions suitable for treatment with the compositions of the present invention include chronic conditions, such as chronic ulcers, diabetic ulcers, and other non-healing (trophic) conditions.

Oncostatin M may be incorporated in physiologically-acceptable carriers for application to the affected area. The nature of the carriers may vary widely and will depend on the intended location of application. For application to the skin, a cream or ointment base is usually preferred, suitable bases include lanolin, Silvadene (Marion) (particularly for the treatment of burns), Aquaphor (Duke Laboratories, South Norwalk, Conn.), and the like. If desired, it will be possible to incorporate Oncostatin M containing compositions in bandages and other wound dressings to provide for continuous exposure of the wound to the peptide. Aerosol applications may also find use.

The concentration of polypeptide in the treatment composition is not critical. The polypeptide will be present in an epithelial cell proliferation-inducing amount. The compositions will be applied topically to the affected area, typically as eye drops to the eye or as creams, ointments or lotions to the skin. In the case of eyes, frequent treatment is desirable, usually being applied at intervals of 4 hours or less. On the skin, it is desirable to continually maintain the treatment composition on the affected area during healing, with applications of the treatment composition from two to four times a day or more frequently.

Oncostatin M finds use with other growth regulatory proteins, particularly those produced by leucocytes, more particularly those factors which have substantial homology with growth regulatory proteins. Preferably the homology is greater than at least about 70%, preferably greater than at least about 90%, of interferons, transforming growth factors, more particularly the transforming growth factors-$\beta$, both one and two, or active fragments thereof and tumor necrosis factor.

For use in culture, the various components of the anti-neoplastic composition may be derived from any vertebrate source, not necessarily the same source as the cells. However, for treatment of a mammal, it will usually be desirable to employ a component which has substantially the same or the same sequence as the naturally occurring component, so as to minimize the potential for an immunogenic response. Usually, the component will differ by fewer than 5 mole percent, more usually by fewer than 2 mole percent from the amino acid sequence of the naturally occurring sequence from the host.

The composition may have two or more components, usually having fewer than six components, directed to anti-neoplastic activity. Besides the Oncostatin M which will usually be present in from about 10, usually at least 25 weight percent, and not more than about 90, usually not more than about 80 weight percent of the inhibiting components, one or more transforming growth factors may be employed, as well as one or more IFNs or tumor necrosis factor may be employed. Thus in particular situations, it may be desirable to use mixtures of related compositions, rather than an individual compound. As already indicated, besides the naturally occurring compounds, active fragments may be employed, as well as chimeras, where a portion of one related molecule is joined to the other portion of another related molecule. See, for example, EPA 32, 134 and corresponding U.S. application Ser. No. 791,247, filed Oct. 25, 1985.

The other growth regulatory compounds may be obtained in a variety of ways. They may be purchased from commercial sources. Alternatively, they are available from naturally occurring sources, particularly conditioned media, where the individual components may be purified employing various purification techniques. These techniques may include solvent extraction, gel permeation chromatography, reversed phase-HPLC, electrophoresis, or the like. For smaller molecules, various synthetic techniques may be employed, where the polypeptide will be synthesized on a solid support. A number of commercial synthesizers are available and may be used to advantage, for example, from Smith-Kline Beckman, Applied Biosystems, etc.

Recombinant techniques may also be employed, where a sequence coding for the particular component or active fragment thereof may be introduced into an expression cassette, which may then be transformed into an appropriate host. Both prokaryotic or eukaryotic hosts may be employed. The particular techniques for isolating or preparing sequences, constructing an expression cassette, transforming the expression cassette into a host, where the expression cassette may be maintained on an extrachromosomal element or integrated into the chromosome of the host, and expression and isolation of the polypeptide product, finds ample exemplification in the literature and need not be expanded upon here. See, for example, U.S. Pat. Nos. 4,530,901; 4,551,433; 4,569,790; 4,582,800; and 4,615,974.

The composition will vary widely depending upon its intended purpose, the desired ratio of the components, as well as the nature of the components and their activity. Thus, depending upon the nature of the cell line, its response to the different components and their synergistic activity, the ratios of the various components will vary. Usually, the amount of Oncostatin M or congener which is employed in combination will be greater than about 0.1% and less than about 50% of the amount of Oncostatin M which would provide the desired activity by itself. For the most part, the amount of Oncostatin M or congener will generally be in the range of about 0.5 to 25% of the amount of Oncostatin M or congener employed by itself. The total amount of transforming growth factors or tumor necrosis factor will generally be in the range of about 0.1 to 50% of the amount of transforming growth factor or tumor necrosis factor employed by itself to achieve the desired activity, usually from about 0.1 to 20%. For the IFN, there is no direct comparison for anti-neoplastic activity. Thus, the amount of IFN will be based on the concentration of IFN which provides the desired level of anti-neoplastic inhibition with a predetermined amount of Oncostatin M.

The concentration of Oncostatin M or congener which may be used in culture will generally be in the range of about 1 to 500 growth inhibitory units/ml (see Experimental Section for definition of units). The concentration of transforming growth factors or tumor necrosis factors that are employed, will generally be from about 1 to 25 growth inhibitory units/ml (see Experimental Section for definition of units), while the concentration of interferon will generally range from about 1 to 90 growth inhibitory units/ml (see Experimental Section for definition of units). Thus, in culture, one can provide for varying degrees of inhibition in the culture by employing different combinations of the various components with varying types of cells in culture and determining the response of the cells in culture to the different compositions. In this manner, one may predict particular combinations which may be used with a mammalian host in the treatment of neoplastic proliferation.

For use in vivo, the subject compositions may be administered in a variety of ways, by injection, by infusion, topically, parenterally, or the like. Administration may be in any physiologically acceptable carrier, such as sterilized water, phosphate buffered saline, saline, aqueous ethanol, etc.

The subject compositions may be formulated in a variety of ways, including in the lumen of liposomes, particularly where the liposomes may be bound to homing molecules targeted for a particular neoplastic cells, e.g., antibodies, nondegradable particle matrices, or the like. Other components may be included in the formulation such as buffers, stabilizers, surfactants, biocides, etc. These components have found extensive exemplification in the literature and need not be described in particular here.

|  | EXPERIMENTAL Table of Contents |
|---|---|
| Example 1: | Methods for Determination of Biological Activity of Oncostatin M, TGF-$\beta$, TNF, and IFN-Y |
|  | A. Growth Inhibition Assay |
|  | B. Cell Growth Modulatory Assay |
|  | C. Soft Agar Colony Inhibition Assay |
|  | D. Inhibition of Growth of Tumors in Nude Mice |
|  | E. Radioreceptor Assay |

EXPERIMENTAL
Table of Contents

| | |
|---|---|
| Example 2: | Isolation and Purification of Oncostatin M, TGF-β1 and IFN-Y from Cultured Cells |
| | A. Isolation of Oncostatin M, TGF-β1, and IFN-Y from Primary Cultures of T-lymphocytes |
| | B. Isolation of Oncostatin M from U937 Cells |
| Example 3: | Physiochemical Properties of Purified Oncostatin M |
| | A. Characterization of Oncostatin M |
| | B. Characterization of Oncostatin M from Human T-lymphocytes |
| Example 4: | Biological Activity of Purified Oncostatin M |
| | A. Inhibition of Tumor Cell Replication |
| | B. Inhibition of Tumor Cell Colony Formation |
| | C. Differential Effect of Oncostatin M on Normal and Transformed Cells |
| | D. Morphological Changes Induced by Oncostatin M |
| | E. Inhibition of Growth of A375 Cells in Nude Mice |
| | F. Receptor Binding Activity |
| Example 5: | Specificity of Antibody to Oncostatin M |
| | A. Peptide Synthesis |
| | B. Production of Antibodies |
| | C. Iodination of Oncostatin M |
| Example 6: | Synergistic Effects of Oncostatin M and Other Growth Factors |
| | A. Oncostatin M, TGF-β1 and rIFN-Y Effects on A375 Cells |
| | B. Oncostatin H and TNF-α Effects on A375 Cells and MCF-7 Cells |
| Example 7: | DNA Cloning and DNA Sequence of Oncostatin M |
| | A. Preparation of cDNA Libraries |
| | B. Restriction Site Mapping of the cDNA Clone |
| | C. The Sequence of 2.1 kb cDNA Clone Encoding Oncostatin M |
| | D. Poly(A+) RNA in Different Cell Types |
| Example 8: | Oncostatin M Expressed in Recombinant Bacteria |
| | A. Preparation and Cloning of Expression Plasmids |
| | B. Preparation of Recombinant Oncostatin M Genes |
| | C. Preparation of Recombinant Proteins |
| Example 9: | Oncostatin M Expressed in Mammalian Cells |
| | A. Preparation and Cloning of Expression Plasmids |
| | B. Preparation of Recombinant Oncostatin M Genes |
| | C. Preparation of Recombinant Oncostatin M |
| Example 10: | Oncostatin M Expressed in Insect Cells |
| Example 11: | Biological Activity of Recombinant Oncostatin M |
| Example 12: | Physiochemical Characterization of Recombinant Oncostatin M |
| | A. SDS-PAGE |

Example 1

Methods for Determination of Biological Activity of Oncostatin M, TGF-β1, TNF and IFN-γ

A. Growth Inhibition Assay

A375 melanoma cells ($4 \times 10^3$ cells/50 μl), Mv1Lu mink lung epithelial cells ($3.5 \times 10^3$ cells/50 μl), or other cell line of interest at an appropriate cell density were subcultured for four hours on flat-bottomed 96-well tissue culture plates (Costar 3596, Cambridge, Mass.) in growth medium comprising Dulbecco's modified Eagle's medium (DMEM), supplemented with 10% heat-inactivated fetal bovine serum, and P/S. Test samples to be assayed for growth inhibition were diluted in growth medium and assayed in triplicate with 50 μl of the diluted sample added to each well. The cells were incubated for 72 hours at 37° C. At the end of this incubation period, each well was treated for 24 hours with 100 μl of growth medium containing 5-[$^{125}$I]iodo-2'-deoxyuridine (0.05 μCi/well (Amersham, Arlington Heights, Ill.). The monolayers were washed with phosphate-buffered saline (PBS), fixed in 95% methanol and air-dried. The [$^{125}$I]iododeoxyuridine incorporated by the cells was solubilized with 200 μl of 1N sodium hydroxide and the amount of cell growth was measured by the amount of [$^{125}$I]iododeoxyuridine incorporated into the DNA of actively growing cells. One unit of activity was defined as the amount of the test sample required to give 50% inhibition of growth of A375 cells relative to untreated cells.

Cytostasis was also estimated by incubating unlabeled target cells with serial dilutions of the test sample in growth medium. After 48 hours, cells were trypsinized and the total number of viable and dead cells was determined by staining with 0.2% trypan blue. The correlation between a decrease in the number of recoverable viable cells and a decrease in the amount of radioactivity incorporated into the DNA of viable cells was calculated.

B. Cell Growth Modulatory Assay Using $^3$H-Thymidine Incorporation into DNA (GIA)

The assays were performed in 96 flat well plates (Costar 3596). Human melanoma cells (A375) ($3 \times 10^3$/100 μl) or cells from another cell line of interest were at an appropriate cell density used. Cells in 100 μl growth medium were placed in each well. Three hours later, 100 μl of test sample in growth medium was added to each well. Plates were incubated at 37° C. for 3 days. Then 25 μl (0.5 μCi) of a solution of $^3$H-thymidine (specific activity 27 μCi/μg) was added to each well for the final 6 hours of incubation. The cells were then transferred to glass filter strips using a multiwell harvester (PHD Cell Harvester, Cambridge Technology, Inc.). The filters were transferred to scintillation vials. Two ml of scintillation fluid (ScientiVerse II, Fisher Scientific Co.) was added and the samples counted in a scintillation counter to quantitate $^3$H-thymidine incorporation.

C. Soft Agar Colony Inhibition Assay (TGI)

A 0.5 ml base layer of 0.5% agar (Agar Noble; Difco Laboratories, Detroit, Mich.) in growth medium was added to 24-well Costar tissue culture plates. One-half ml 0.3% agar in growth medium containing 1 to $2.5 \times 10^3$ A375 cells or other cell line of interest at an appropriate cell density, and various concentrations of the factor to be tested were overlaid on the base layer of agar. The plates were incubated at 37° C. in a humidified atmosphere of 5% $CO_2$ in air and refed after 7 days by addition of 0.5 ml of 0.3% agar in growth medium containing the same concentration of the factor to be tested as used previously. Colonies were enumerated unfixed and unstained. The number of colonies with greater than 6 cells were scored.

D. Inhibition of Growth of Tumors in Nude Mice

A375 tumor cells ($2.3 \times 10^6$) or an appropriate number of cells of another cell line of interest were injected subcutaneously in the interscapular region of nude mice. When the tumors became palpable, half of the mice were inoculated subcutaneously proximal to the tumor with either (a) 100 μl PBS containing 1.6 μg bovine serum albumin (BSA) or (b) 100 μl PBS containing 1.6 μg BSA plus the test sample. The mice were inoculated in the same manner every 2–3 days until about 19 days after the first inoculation. The diameter and width of each tumor was measured every 2–3 days using calipers.

E. Radioreceptor Assay

Oncostatin M was purified to homogeneity from TPA-treated U937 cells (see Example 2B), and radiolabeled with $^{125}$I by the iodogen method (Pierce Chemical Co.) The iodinated protein retained approximately 85% of its original biological activity as determined by growth inhibition assays.

The cell line of interest was plated in 48-well plates at a density of $2 \times 10^5$ cells/well and maintained at 37° C. for 16–24 hours before initiation of the assay. Cell monolayers were then washed once with Binding buffer (Linsley et al., *Biochemistry* (1986) 25:2978–2986). To measure total binding, $^{125}$I-Oncostatin M was added at concentrations ranging from 0.5–100 ng/ml. To measure non-specific binding, unlabeled Oncostatin M was added simultaneously with the $^{125}$I-Oncostatin M to replicate plates at a concentration 20- to 100-fold higher than the concentration of $^{125}$I-Oncostatin M. Binding was allowed to proceed for 2–5 hours at 23°, then the monolayers were washed four times with Binding Buffer, cell-bound radioactivity was solubilized with 1N NaOH and was counted in a gamma counter. Specific binding was calculated by subtracting the non-specific binding from total binding. The dissociation constant ($K_d$) and binding capacity was determined by Scatchard analysis (Scatchard, *Ann. N.Y. Acad. Sci.* (1949) 51:660).

Example 2

Isolation and Purification of Oncostatin M, TGF-β1, and IFN-γ from Cultured Cells A. Isolation of Oncostatin M, TGF-β1, and IFN-γ from Primary Cultures of T-lymphoblasts 1. Cell culture.

Leukofractions, containing mononuclear cells, were separated from buffy coats of blood from normal adult volunteers (Puget Sound Blood Center, Seattle, Wash.). Mononuclear cells were isolated by isopyenic centrifugation with Ficoll-Hypaque. Interface cells were collected and platelets removed with thrombin (0.5 U/ml) in the presence of 1 mM $Ca^{2+}$, $Mg^{2+}$. To deplete monocytes and B-cells, cells adherent to plastic surfaces or nylon wool were removed. The resulting peripheral blood lymphocytes (PBL) consisted of 94% T-cells, fewer than 0.5% B-cells, and 5% monocytes. Primary T-lymphoblasts can be maintained in culture for up to four weeks by restimulation every third day with phytohemagglutinin (PHA) (2 μg/ml) and T-cell-specific monoclonal antibody MAb9.3 (Ledbetter et al., *J. Immunol.* (1985) 135:2331–2336). At the end of the culture period, more than 95% of the cells are still viable. This method of T-lymphocyte propagation yeilds a cell population essentially free of monocytes/macrophages and provides a 99% pure T-cell-derived conditioned medium.

PBL obtained as described above were activated with PHA (2 μg/ml) for 96 hours in chemically-defined medium supplemented with bovine serum albumin-linoleic fatty acid conjugate (200 mg/l). This collection of supernatant fluid was discarded. Following primary activation, non-adherent lymphoblasts were adjusted to $1 \times 10^6$/ml in fresh chemical-defined medium containing bovine serum albumin-linoleic fatty acid conjugate and restimulated with PHA (0.5 μg/ml) and monoclonal antibody MAb 9.3 (1 μg/ml) at 37° C., 5% $CO_2$ for 72 hours. Seventy-two-hour collections were taken for four weeks. The serum-free conditioned medium was collected, clarified by centrifugation and concentrated by ultrafiltration (Amicon Diaflo membrane YM-10, 10,000 molecular weight cutoff; Amicon Corp., Danvers, Mass.). The concentrated PBL supernatant activated was the starting material for the purification of TGF-β1, γ-IFN, and Oncostatin M.

2. Purification by reversed phase HPLC.

The concentrated supernatant from activated PBL was dialyzed against 0.1M acetic acid, lyophilized, and reconstituted in 0.1M acetic acid subjected to gel permeation chromatography on Bio-Gel P-60 ($2.5 \times 88$ cm Bio-Rad Laboratories, Richmond, Calif.) and equilibrated with 1M acetic acid at 20 ml/hr. Fractions comprising the major growth inhibitory activity were pooled. The bulk of contaminating protein was eluted in the exclusion volume of the column and was separated from the A375 growth inhibitory activity. A major peak of anti-proliferative activity against A375 cells, with a molecular weight range between $M_r$ 14,000 to 28,000 was found. Fractions with growth inhibitory activity were pooled and lyophilized.

The P-60 pool was reconstituted in 0.05% TFA in water. Further purification of TGF-β1, γ-IFN, and Oncostatin M was achieved by reversed-phase HPLC. The separations were performed on a preparative μ Bondapak $C_{18}$ column (10 μm particle size $7.8 \times 300$ mm; Waters, Milford, Mass.) at room temperature. The primary mobile phase was 0.05% aqueous trifluoroacetic acid, and the secondary mobile phase was acetonitrile containing 0.045% trifluoroacetic acid. The concentration of acetonitrile was increased linearly (0.083% per min) during 240 min at a flow rate of 2.0 ml/min at room temperature for elution of proteins.

Three peaks of activity were found to be well resolved from each other. Only 33% of the initial activity was recovered. GIF-1 eluted at 33% acetonitrile and contained 10% of the recovered activity; GIF-2 eluted at 38% acetonitrile, representing 13% of the recovered activity; and GIF-3 eluted between 40 and 42% acetonitrile containing approximately 77% of the total recovered activity. The major activity peaks were pooled as indicated and subsequently characterized.

3. Further purification by reversed phase HPLC.

TGF-β1-containing fractions were rechromatographed on an analytical μ Bondapak $C_{18}$ column ($3.9 \times 300$ mm) with 1-propanol containing 0.035% trifluoroacetic acid as the mobile-phase modifier. The 1-propanol concentration was increased linearly (0.028% per min) during 6 hours at a flow rate of 0.2 ml/min.

γ-IFN-containing fractions were rechromatographed on an analytical μ Bondapak $C_{18}$ column and subsequently on an analytical $C_4$ Vydac column (330-A pore size, The Separations Group, Hesperia, Calif.) with 1-propanol containing 0.035% trifluoroacetic acid for elution. The 1-propanol concentration was increased linearly (0.028% per min) during 360 min at a flow rate of 0.2 ml/min at room temperature for elution of proteins.

Oncostatin M-containing fractions were rechromatographed on an analytical μ Bondapak $C_{18}$ column and subsequently on an analytical $C_4$ Vydac column with 1-propanol containing 0.035% trifluoracetic acid for elution. The gradient conditions and flow rate were the same as described for the purification of γ-IFN. Purified Oncostatin M was analyzed by sodium dodecyl-sulfate polyacrylamide gel electrophoresis, and was assayed for growth inhibitory activity on A375 cells and Mv1Lu cells. Oncostatin M used in synergy experiments was approximately 80% pure. The dose-response and synergy characteristics of this preparation of Oncostatin M were identical to homogenous Oncostatin M isolated from the conditioned medium of macrophage-like cells and purified by reversed-phase HPLC (Zarling et al., Proc. Natl. Acad. Sci. USA (1986) 83:9739–9743).

B. Isolation of Oncostatin M from U937 Cells

1. Cell culture.

U937 cells, a histiocyctic lymphoma cell line (Sundstrom and Nilsson, Int. J. Cancer (1976) 17:565–577), were cultured in 850 $cm^2$ roller bottles (Corning C2540) at a concentration of $4 \times 10^5$ cells/ml in a total volume of 300 ml RPMI 1640 medium supplemented with 10% fetal calf serum (FCS), penicillin/streptomycin (PS), L-glutamine and 10 ng/ml 12-o-tetradecanoylphorbol 13-acetate (TPA). Four days later, the supernatants containing the FCS and TPA were removed, the roller bottles were washed five times with serum-free RPMI-1640, and the cells which detached ($1 \times 10^5$ cells/ml) were washed 3 times with serum-free medium and added back to the bottles, resulting in a final volume of 125 ml serum-free RPMI-1640 medium per roller bottle. One day later, the supernatants were collected, centrifuged to remove the cells, filtered through 0.45 micron (μ) Nalgene filter and concentrated using a hollow fiber system (Amicon cartridge HIP10-20) to a volume of 150 ml (initial volume 1500 ml). Oncostatin M was also isolated from supernatants of serum-free TPA-treated U937 cells in 150 $cm^2$ tissue culture flasks. The supernatant was concentrated with an Amicon Diaflo membrane PM-10, 10 kD cut-off and dialyzed. Following dialysis, the concentrate was diluted with acetic acid resulting in a final concentration of 0.1N acetic acid in 500 ml and concentrated to 50 ml using an Amicon PM-10 filter. The 50 ml concentrate was diluted to 400 ml with 0.1N acetic acid and concentrated to 40 ml with the same filter. The concentrate was diluted with 1N acetic acid and the resulting precipitate was removed by centrifugation. The resulting concentrate was frozen and lyophilized. The lyophilized material was used for purification steps.

2. Purification by gel permeation chromatography.

A Bio-Sil TSK-250 column ($600 \times 21.5$ mm) (BioRad) was attached to a high pressure liquid chromatographic system. The crude fraction (10 mg/ml) was dissolved in 40% acetonitrile in 0.1% aqueous trifluoroacetic acid (0.1% TFA). A 2 ml aliquot of the mixture was injected and elution was performed isocratically with a mobile phase of 40% acetonitrile in 0.1% TFA. The flow rate was 2.5 ml/min and chart speed was set at 0.25 cm/min. Five ml fractions were collected. The chromatography was performed at room temperature. An aliquot from each fraction was evaporated and assayed in triplicate for growth inhibitory activity (GIA) of A375 cells.

The active fractions (Fractions 21 and 22) from six runs were pooled. The pooled material had a total of approximately $4.8 \times 10^5$ GIA units. The factor was found to have an apparent molecular weight of 18 kD as determined by size exclusion chromatography (Bio-Sil TSK-250 column).

3. Purification by reversed phase HPLC of TSK-250 fractions.

Pooled TSK-250 fractions 21 and 22 described above were diluted two-fold with 0.1% TFA. This mixture was injected isocratically on a μ-Bondapak-C18 column ($7.8 \times 300$ mm) (referred to as $C18^1$) at room temperature. The flow rate was set at 2.0 ml/min and the chart speed was 0.25 cm/min. The linear gradient was used between primary solvent 0.1% TFA and the secondary solvent acetonitrile-TFA 0.1%. The gradient conditions were 0–30% in 20 min; then 30–45% in 150 min; 45–55% in 20 min; and 55–100% in 10 min. All solvents were HPLC grade. Four ml fractions were collected and aliquots of each fraction were assayed for growth inhibitory activity. Fractions 72–75 were found to contain the majority of activity. The active fractions eluted between 41–52% of acetonitrile concentration.

Fractions 72–75 were pooled. Sixteen ml of 0.1% TFA was added to the pooled fractions. The mixture was injected into a μ-Bondapak-C18 column ($3.9 \times 300$ mm) (referred to as $C18^2$) at room temperature. The flow rate was set a 1 ml/min and chart speed was 0.25 cm/min. The gradient conditions were 0–35% in 10 min; 35–45% in 100 min; and 45–100% in 10 min. were collected and aliquots were taken and assayed for GIA. Most of the activity emerged from the column between 40.7 to 41.3% acetonitrile concentration (retention time 83–86min).

Active fractions were pooled and diluted two-fold with 0.1% TFA and injected isocratically on a μ-Bondapak-C18 column.($3.9 \times 300$ mm) (referred to as $C18^3$) at room temperature. The flow rate was 1 ml/min and chart speed was 0.25 cm/min. A linear gradient was used between primary solvent 0.1% TFA and the secondary solvent n-propanol-TFA (0.1%). The gradient conditions were 0–23% in 20 min and 23–35% in 120 min. Fractions were collected and aliquots of each fraction were assayed for GIA. Most of the activity appeared between 25–26.5% propanol concentration (retention time 59 min). This apparently homogeneous fraction contained approximately 300 ng protein and about 40,000 GIA units.

Example 3

Physicochemical Properties of Purified Oncostatin M

A. Characterization of Oncostatin M

1. Amino acid sequence determination.

Automated sequence analysis of unmodified Oncostatin M isolated from supernatants of serum-free TPA-treated U937 cells in 150 $cm^2$ tissue culture flasks by cleavage with endoproteinase Lys-C was performed on a Model 470A amino acid sequencer (Applied Biosystems, Foster City, Calif.

The N-terminal sequence and internal fragments of Oncostatin M was determined by microsequence analysis of the reduced and S-pyridinethylated polypeptide and of peptides obtained from enzymatic digests of reduced and S-pyridinethylated Oncostatin M with the endoproteinase Lys-C and *Staphylococcus aureus* V8 protease. The peptide fragments were purified by reverse phase HPLC, using volatile solvents. The peptides were subjected to automated repetitive Edman degradation in the Model 470A protein sequencer (Applied Biosystems, Inc.). The phenylthiohydantoin amino acids were analyzed by reverse phase HPLC (Applied Biosystems, Inc.) with a PTH-C18 column (2.1×220 mm, ABI), using a sodium acetate buffer/tetrahydrofuran/acetonitrile gradient for elution.

A comparison of this sequence with those stored in the current protein data base (PIR Release 13.0, 1987), revealed no significant sequence homologies with any other known sequence. In addition, there is no homology with tumor necrosis factor, lymphotoxin, colony stimulating factor, interleukin 1 or 2 or β-transforming growth factor.

2. SDS-PAGE of Oncostatin M.

Figure 2:
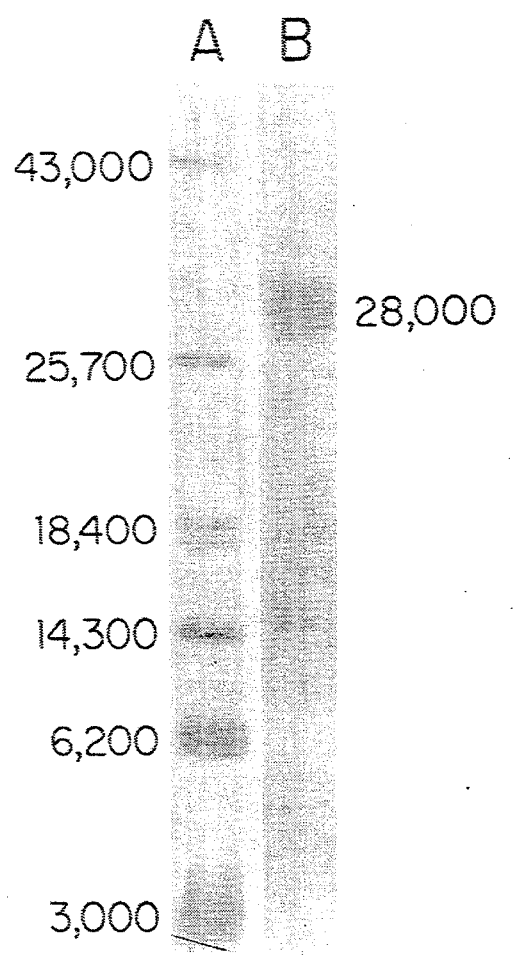
FIG. 2 is a photograph of an SDS-PAGE analysis of Oncostatin M.

Purified Oncostatin M, subjected to SDS-PAGE performed under reducing conditions, was found to have an apparent molecular weight of approximately 28 kD as shown in FIG. 2. The following proteins were used as standards (lane A): ovalbumin, $M_r$=43 kD chymotrypsinogen α, $M_r$=25.7 kD; lactoglobulin β, $M_r$=18.4 kD; lysozyme, $M_r$=14.2 kD; bovine trypsin inhibitor $M_r$=6.2 kD; insulin A and B chain, $M_r$=2.3 kD and 3.4 kD respectively. Oncostatin M was applied to lane B.

Oncostatin M, subjected to PAGE under non-reducing conditions, also has an apparent molecular weight of 28 kD and protein electroeluted from the band was found to inhibit proliferation of A375 cells.

3. Effect of various treatments on Oncostatin M.

U937 cells (RPMI 1640+5% FCS seeded at 7.5×10⁵ cells/ml) were treated with TPA (10 ng/ml) for 3 days. The cells were then washed with medium (serum-free RPMI 1640) and incubated for 24 hr in serum-free (serum-free RPMI 1640) medium before collecting the supernatants. The supernatants were treated with 1N acetic acid or 1N ammonium hydroxide. They were then dialyzed against medium (serum-free RPMI 1640) and tested for their ability to inhibit ³H-thymidine incorporation into A375 cells using the assay as described in Example 1B

TABLE 1

Effect of Various Treatments of Supernatants of TPA-Induced U937 Cells on Tumor Growth Inhibitory Activity

| Treatment | Final Dilution of Supernatant | | | |
|---|---|---|---|---|
| | 0 | 1:4 | 1:8 | 1:16 |
| Medium Alone | 39,780* | — | — | — |
| Untreated Super. | — | 7,206 | 13,896 | 16,000 |
| 1 N Acetic Acid | — | 6,670 | 17,073 | 18,783 |
| 1 NH₄OH | — | 6,956 | 15,016 | 13,923 |

*Data shown are ³H-TdR incorporation (counts per minute.)

The above results demonstrate that Oncostatin M in the dialyzed supernatant is substantially resistant to inactivation by 1N acetic acid and 1N ammonium hydroxide. Thus, the subject compounds are relatively insensitive to both moderately strong acid and moderately strong base.

The subject compound was also tested for heat stability and was found to retain its activity after exposure to 56° C. for 1 hr, but to lose substantially all its activity after exposure to 95° C. for 30 min.

4. Carbohydrate composition of Oncostatin M.

The carbohydrate composition of Oncostatin M was examined by testing for glycosidase sensitivity. Immune precipitates prepared as in Example 5, below were treated with buffer, endoglycosidase H, or neuraminidase (Linsley et al., Biochemistry (1986) 25:2978-2986). Treatment with endoglycosidase H, an enzyme with specificity for N-linked high mannose oligosaccharides resulted in the appearance of a lower molecular weight species of Mr=24 kD. Only a portion of the radiolabeled material was sensitive to this enzyme, indicating that not all molecules contained high mannose oligosaccharides. Treatment with neuraminidase resulted in the appearance of a single band of $M_r$=27 kD, indicating that the heterogeneity in size of untreated ¹²⁵I-labeled Oncostatin M was due to molecular heterogeneity in sialyation of the glycoprotein core. The results indicated that active preparations of Oncostatin M contained a mixture of high mannose and complex N-linked oligosaccharide side chains.

B. Characterization of Oncostatin M from Human T-lymphocytes

1. Amino acid sequence determination.

Two aminoterminal sequences were determined by automated Edman degradation for the Oncostatin M preparation. Unambiguous identification of phenylthiohydantoin derivatives of amino acids was possible up to residue 19 for the major sequence, except at positions 5, 6, 7, 11, 14, and 15. The amino-terminal sequence of Oncostatin M read as follows:

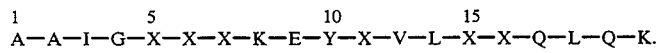

Identified phenylthiohydantoin derivatives of amino acids up to residue 19 were identical with those established for the N-terminal sequence of Oncostatin M derived from phorbolester-induced U937 histocytic lymphoma cells (see above, Example 3A1).

2. SDS-PAGE.

The purity of the final Oncostatin M preparation was determined by sodium dodecyl sulfate-polyacrylamide gel electrophoresis under reducing conditions. The preparation remained slightly contaminated by a higher molecular weight protein. The major polypeptide band had an $M_r$ of 28,000.

Example 4

Biological Activity of Purified Oncostatin M

A. Inhibition of Tumor Cell Replication

The effect of Oncostatin M on various cell lines was assessed using a cell growth modulatory assay performed as described in Example 1B, above. The cell lines tested included A549 lung cancer cells, HTB10 neuroblastoma cells, and A375 melanoma cells. The results are as shown in Table 2.

TABLE 2

Inhibition of Replication of Tumor Cells
by Purified Oncostatin M from U937 Cells

| Tumor Cells | GIA Units* to Cause 30% Inhibition $^3$H-TdR Incorporation |
|---|---|
| A549 (lung cancer) | 21.0 |
| HTB10 (neuroblastoma) | 81.0 |
| A375 (melanoma) | 0.3 |

*One unit tumor growth inhibitory activity (GIA) is defined as that amount which causes 50% inhibition of $^3$H-TdR incorporation into A375 melanoma cells using the assay described in Example 1B.

Based upon the specific activity of purified Oncostatin M it was determined that the concentration (ng/ml) to cause 30% inhibition $^3$H-TdR into A549, HTB10 and A375 cells was approximately 1.4, 4.0, and 0.015 ng/ml, respectively.

B. Inhibition of Tumor Cell Colony Formation

A375 cells were plated in soft agar, with or without the indicated GIA units of Oncostatin M (see Table 3), as described above in Example 1C. The factor used was from a C18$^3$ propanol column fraction with peak tumor growth inhibitory activity (GIA). The number of colonies was enumerated at 11 days.

TABLE 3

Inhibition of A37 5 Melanoma Cell
Colony Formation Soft Agar by Purified
Oncostatin M Isolated from U937 Cells

| GIA Units*/Well | # Colonies | % Inhibition of Colony Formation |
|---|---|---|
| 250 | 4 | 96 |
| 83 | 6 | 94 |
| 27 | 11 | 89 |
| 45 | 32 | 69 |
| 0 | 106 | — |

*One GIA unit was defined as the concentration of Oncostatin M which causes 50% inhibition of $^3$H-thymidine incorporation into A375 cells using the assay described in Example 1B.

C. Differential Effect of Oncostatin M on Normal and Transformed Cells

Human tumor cells (A375 melanoma cells, A549 lung cancer cells, HBT10 neuroblastoma cells, and SK-MEL28 melanoma cells) were seeded at $3 \times 10^3$ cells/well and normal fibroblasts (WI26 cells and WI38 cells) at $1.5 \times 10^3$ cells/well in 96-well plates. Various concentrations of purified Oncostatin M, obtained from the fraction from the C18$^3$ column with peak antiproliferative activity against A375 cells were used. The assay was performed as described in Example 1B above. The results are shown in Table 4.

TABLE 4

Effect of Oncostatin M on Proliferation
of Tumor Cells and Normal Fibroblasts*

| GIA** units/well | % Inhibition | | % Stimulation |
|---|---|---|---|
| Exp. 1 | A375 | | WI38 |
| 16 | 83 | | 25 |
| 4 | 62 | | 30 |
| 1 | 46 | | 46 |
| Exp. 2 | A375 | HTB10 | WI26 |
| 27 | NT | 28 | 46 |
| 9 | 87 | 22 | 36 |
| 3 | 76 | 11 | 52 |
| Exp. 3 | A375 | A549 | |
| 75 | 89 | 30 | |
| 25 | 85 | 22 | |
| 8 | 71 | 16 | |
| Exp. 4 | A375 | SK-MEL28 | |
| 20 | 87 | 44 | |

TABLE 4-continued

Effect of Oncostatin M on Proliferation
of Tumor Cells and Normal Fibroblasts*

| GIA** units/well | % Inhibition | % Stimulation |
|---|---|---|
| 5 | 75 | 25 |
| 1 | 59 | 11 |

*Results shown are % inhibition or % stimulation of $^3$H-thymidine incorporated.
**One GIA unit the amount of Oncostatin M that causes 50% inhibition of $^3$H-thymidine incorporation into A375 cells.

Results in Table 4 indicate that Oncostatin M inhibited replication of tumor cells, but did not inhibit replication of normal cells. Rather, it actually stimulated growth of the normal cells.

The ability of PBL-derived Oncostatin M to affect replication of a variety of cells was also investigated. Mouse L929 cells were insensitive to PBL-derived Oncostatin M using up to 1000 GIA units/ml. Growth of human fibroblast, WI26, was stimulated by treatment with 1000 GIA units/ml. Normal human T-lymphocyte proliferation at 72 hours post mitogenesis was not affected by up to 500 GIA units/ml.

D. Morphological Changes Induced by Oncostatin M

In addition to the differential effect on $^3$H-thymidine incorporation into tumor cells and normal human fibroblasts, a differential effect on morphology and cell number following 3 days of treatment of the two cell types with Oncostatin M was also observed, as shown in FIG. 1.

The Oncostatin M used was from the HPLC-C18$^3$ column fraction with peak activity for inhibiting proliferation of A375 cells. FIG. 1 is a series of photomicrographs of A375 melanoma cells that were untreated (A), treated with 5 growth inhibitory activity (GIA) units of Oncostatin M (B), or 100 units (C). Photomicrographs of WI38 fibroblasts that were untreated (D), treated with 5 units GIA (E), or 100 units (F). The cells were stained with crystal violet in 0.5% methanol. Magnification=63X.

E. Inhibition of Growth of A375 Cells in Nude Mice

Six nude mice were injected with A375 cells as described in Example 1D, above. After the tumors became palpable, the mice were injected, proximal to the tumor, with PBS (control) or PBS containing 400 ng Oncostatin M, three mice in each group.

The cumulative sizes (mm$^2$) of the tumors in each group of three mice were determined every 2–3 days. The cumulative size of the tumors is shown in Table 5, and the tumor weights after 21 days are shown in Table 6.

TABLE 5

| Days After Treatment | Cumulative Tumor Size (mm$^3$)* | |
|---|---|---|
| | PBS | Oncostatin M |
| −1 | 30 | 30 |
| 0 | 70 | 50 |
| 3 | 116 | 64 |
| 5 | 130 | 66 |
| 7 | 160 | 90 |
| 10 | 180 | 88 |
| 12 | 210 | 100 |
| 14 | 268 | 116 |

The tumors in mice treated with Oncostatin M were only about half the size of those in control animals.

In Table 6 are shown the weight of the tumors (in mg) from each of the mice described above. The tumors isolated from the Oncostatin M treated mice were approximately one-third the weight of the tumors from the control-treated mice.

TABLE 6

| Mouse No. | Treatment | Tumor Wt (mg) |
| --- | --- | --- |
| 96 | PBS | 540 |
| 93 | PBS | 440 |
| 92 | PBS | 480 |
| 94 | Oncostatin M | 100 |
| 97 | Oncostatin M | 140 |
| 95 | Oncostatin M | 200 |

F. Radioreceptor Assay

1. Dissociation constant and receptor concentration.

Binding of Oncostatin M to a membrane receptor was demonstrated using the radioreceptor assay described in Example 1E. The human tumor cells tested included A375 (melanoma); A875 (melanoma); Me1109 (melanoma); T24 (bladder carcinoma); A549 (lung adenocarcinoma); H2981 (lung adenocarcinoma); H1477 (melanoma); Me180 (melanoma); and MCF (breast). Binding of $^{125}$I-Oncostatin M was specific and saturable, and was not inhibited by other known polypeptide growth regulators (see below). Scatchard analysis of binding data obtained with different cell lines revealed that $^{125}$I-Oncostatin M bound to $1-2 \times 10^4$ binding sites per cell with a $K_d$ of approximately $10^{-9}$M.

2. Specificity of Oncostatin M Receptor.

The specificity of the Oncostatin M receptor was determined by evaluating the ability of several other polypeptide growth factors to compete for binding of $^{125}$I-Oncostatin M (at 30–50 ng/ml) to A375 or A549 cells. The growth factors tested included: tumor necrosis factor-α (20 μg/ml); interleukin 1-β (50 μg/ml); gamma interferon (2.5 μg/ml); epidermal growth factor (2.5 μg/ml); fibroblast growth factor (2.5 μg/ml); transforming growth factor type β (2.5 μg/ml); porcine insulin (2.5 μg/ml); chemotactic peptide (formyl-M-L-F, 50 μM; Lys$^3$ bombesin (50 μM); and Tyr$^3$-bombesin (1 μM). None of these showed significant inhibitory activity towards binding of $^{125}$I-Oncostatin M.

3. SDS-PAGE Analysis.

To identify the Oncostatin M receptor, $^{125}$I-Oncostatin M was chemically cross-linked to its receptor using disuccinimidyl suberate. When the reaction products were examined by SDS PAGE, a single cross-linked complex of $M_r \sim 180,000$ was observed. This complex was observed with several cell lines.

Example 5

Specificity of Antibody to Oncostatin M

A. Peptide Synthesis

A peptide corresponding to residues 6-19 of the Oncostatin M protein was synthesized by solid phase techniques on a Beckman automated instrument as described (Gentry et al., *J. Biol. Chem.* (1983) 258:11219). The peptide was cleaved from the resin using the "low-high" HF procedure (Tam et al., *J. Amer. Chem. Soc.* (1983) 105:6442–6445). Purification was accomplished by preparative HPLC.

B. Production of Antibodies

The peptide was coupled to bovine γ-globulin as described (Gentry and Lawton, *Virology* (1986) 152:421–431). New Zealand white rabbits were primed and boosted (5 times) at 4 sites subcutaneously as described (Gentry and Lawton, *Virology* (1986) 152:421–431). Antisera used were obtained 2 weeks after the fifth boost.

C. Iodination of Oncostatin M

A sample of partially purified Oncostatin M was radiolabeled with iodine-125 using published procedures (Linsley et al., *Proc. Natl. Acad. Sci. USA* (1985) 82:356–360). An aliquot of the labeled preparation containing 100,000 cpm was mixed with rabbit antiserum directed against the N-terminal 17 amino acids of Oncostatin M (final dilution of 1:20), in the absence or presence of the N-terminal peptide (the N-terminal 17 amino acids of Oncostatin M) (2 μg) and subjected to immune precipitation analysis as described (Linsley et al., *Biochemistry* (1986) 25:2978–2986).

Specifically, one tube containing 5 μl was preincubated with 2 μg of the N-terminal peptide in 10 M1 TNEN (20 mM Tris pH 7.5, 5 mM EDTA, 150 mM NaCl, 0.05% Nonidet P-40) containing 0.1% BSA for 30 minutes at 4° C. prior to the addition of $^{125}$I-Oncostatin M in 85 λ TNEN containing 0.1% BSA and 40 mM dithiothreitol (DTT). Seven tubes containing 5 μl antisera were incubated with $I^{125}$ Oncostatin M in 85 μl TNEN containing 0.1% BSA and 40 mM DTT for 30 minutes at 4° C. prior to the addition of 50 μl of 10% formalin-fixed *Staphylococcus aureus* (Pansorbin, Calbiochem).

Following an additional incubation for 30 min at 4° C., the tubes were microfuged and the pellets were washed 4 times with 1 ml TNEN prior to subjecting them to PAGE analysis. A diffuse band of $M_r=32$ kD was observed after SDS/PAGE analysis of the immune precipitates. Precipitation of this species was inhibited by the inclusion of an excess of unlabeled peptide corresponding to the N-terminal 17 amino acids of Oncostatin M, indicating that the precipitation was specific for this peptide.

Example 6

Synergistic Effects of Oncostatin M and Other Growth Factors

A. Oncostatin M, TGF-β1 and rIFN-γ Effects on A375 Cells

The growth inhibitory activity of highly purified TGF-β1, recombinant gamma-interferon (rIFN-γ), and Oncostatin M on A375 cells was determined, and possible synergy between TGF-β1 and Oncostatin M, TGF-β1 and rIFN-γ, and Oncostatin M and rIFN-γ in inhibiting A375 proliferation was tested. IGF-β1 is expressed in units of Mv1Lu growth inhibitory activity, rIFN-γ in units of anti-viral activity and Oncostatin M in units of A375 growth inhibitory activity. Concentrations of TGF-β1 (1–30 U/ml) and Oncostatin M (0.15–10 U/ml) were chosen which caused either no or only minimal growth inhibition when tested individually.

Synergistic responses to simultaneous inhibition with TGF-β1 and Oncostatin M occurred in all combinations tested, with the degree of enhancement ranging from 2.5-3.1 times the expected, additive response. For example, cell proliferation was inhibited approximately 48% by 3.4 U/ml of TGF-β1 and 1.8 U/ml of Oncostatin M, which individually inhibited cell growth by 7 and 12%, respectively. The predicted additive effect would be 19%. The actual response measured was 2.5 times higher. To determine whether the antiproliferative activity of TGF-β1 was truly synergistic with that of Oncostatin M, data from 5 dose combinations were plotted in an isobologram. In this graphic analysis (not shown), the observed marked departure of the line connecting the experimental points below the line for additive effect was indicative of synergistic interaction. An additive antiproliferative response was observed when combinations of Oncostatin M (1–5 U/ml) and IFN-γ (1 to 10 U/ml) were simultaneously added to A375 cells.

B. Oncostatin M and TNF-γ Effects on A375 and MCF-7 Cells

Inhibition of $^3$H-TdR incorporation into A375 cells and MCF-7 cells were compared using the assay described in Example 1B, above. The cells were treated with either Oncostatin M alone, TNF-α (Amgen Biologicals, human recombinant TNF-α) alone, or with a combination of Oncostatin M and TNF-α.

TABLE 7

| Treatment | Observed* % Inhibition of $^3$H-TdR Incorporation | |
|---|---|---|
|  | A375 Cells | MCF-7 Cells |
| Oncostatin M | 17 | 18 |
| TNF-α | 7 | 30 |
| Oncostatin M plus TNF-α | 48 | 79 |

*Calculated % inhibition for the two factors together (additive effect) was 24% and 48% for the A375 cells and MCF-7 cells, respectively.

Table 7 above shows results of in vitro inhibition of replication of A375 cells (measured by inhibition of $^3$Hthymidine incorporation) by Oncostatin M alone, TNF-α alone, and a mixture of both factors. As shown, treatment of A375 cells with a mixture of Oncostatin M and TNF-α gave a greater degree of inhibition of replication of A375 cells than did either factor alone and a greater degree of inhibition than that expected based on the additive levels of inhibition of each factor separately.

Table 7 also shows results of inhibition of in vitro replication of MCF-7 breast tumor cells (measured by inhibition of $^3$H-thymidine incorporation) by Oncostatin M alone, TNF-α alone, and a mixture of both factors. Treatment of MCF-7 breast tumor cells with a mixture of Oncostatin M and TNF-α gave a greater degree of inhibition of replication of MCF-7 breast tumor cells than did either factor alone and a greater degree of inhibition than that expected based on the additive levels of inhibition of each factor separately.

The above results show that Oncostatin M and tumor necrosis factor are synergistic in inhibiting replication of certain tumor cells.

Example 7

DNA Cloning and DNA Sequence of Oncostatin M

A. Preparation of cDNA Libraries

Poly(A)+ RNA obtained from U937 cells treated with media containing phorbol 12-myristate 13-acetate PMA (10 ng/ml) for 16, 36, and 52 hours was pooled and used for cDNA synthesis and cloning into a λgt 10 vector, essentially as described by Huynh et al., *DNA Cloning Techniques: A Practical Approach*, D. Glover (ed) (1984). Briefly, 10 μg poly(A+) RNA was reverse transcribed in the presence of 50 pmol oligo dT. The second strand was synthesized using DNA polymerase I and the cDNA was treated with S1 nuclease to eliminate the hair pin loop. The cDNA was then dG tailed by treatment with terminal deoxy nucleotidyl transferase. The dG tailed cDNA was subsequently chromatographed on Biogel A-50 column to eliminate cDNA smaller than 300 bp. The sized dG tailed cDNA were ligated into EcoRI cut λgt 10 in the presence of single stranded 16 nucleotide-long linker molecule comprising, from the 5' end, AATT followed by 12 deoxycytosine residues (Webb et al., 1987). The ligated DNA was packaged in vitro (Grosveld et al., *Gene* (1981) 13:227–237) and the phage was used to infect *E. coli* C60 Hfl+. This technique gave $3 \times 10^6$ recombinants/μg cDNA. Nitrocellulose filter plaque lifts were done in duplicate and the filters were probed using long, best guess 35 to 50 nucleotide long probes. The oligonucleotide probes were derived from the peptide sequences obtained by automated repetitive Edman degradation. The purified Oncostatin M sequence was either derived from the N-terminal of the protein or by sequencing the protease-generated lysine peptides.

Initial screening of the λgt 10 library was done using a 50 mer oligonucleotide probe. The probe was derived from the lysine peptide.

Peptide 1:

```
  (K)  A   Q   D   L   E   R   S   G   L   N   I   E   D   L   E   K
3' TTC CGG GTC CTG GAC CTC GCC AGA CCG GAC TTG TAA CTC CTG GAC CTC TT 5'
```

λgt 10 clones showing positive reactivity to [$^{32}$P]-labeled above oligonucleotide were plaque purified. Eight clones were obtained. Southern blot analysis showed that the positively reacting cDNA inserts in the clones ranged between 600 bp to 2 Kb. Subsequently, Southern blots were done using a 35 mer oligonucleotide (encoding amino acids 53–64) and a 41 mer oligonucleotide (encoding amino acids 22–35). Only one clone showed positive reactivity with all three radiolabeled oligonucleotide probes.

The cDNA insert of the λgt 10 clone (λOM) was found to be approximately 2.1 Kb. The cDNA insert flanked by EcoRI sites at 5' and 3' ends was subcloned in the EcoRI site of the polylinker region of the plasmid vector pEMBL18 (Dente et al., *Nucleic Acid Res.* (1983) 11:1645–1655. The recombinant was termed pOncM46.

B. Restriction Site Mapping of the cDNA Clone

A restriction map of the clone pOncM46 coding Oncostatin M protein was obtained by standard single or double digestions of the plasmid DNA. The coding region has four PstI sites, a BglII site and a SmaI site.

C. The Sequence of 2.1 kb cDNA Clone Encoding Oncostatin M

The entire nucleotide sequence of the 2.1 Kb clone pOncM46 has been determined (see FIG. 3). The open reading frame starts at nucleotide 253, the stop codon being at nucleotide 1070. The open reading frame has 10 amino acids upstream from the putative initiating methionine. There is one more methionine two amino acids upstream from the assigned initiating methionine.

Nucleotide sequencing coding for both the first and the second methionine in the open reading frame do not agree with the consensus sequence for the initiating methionine (Kozak, *Cell* (1986) 44:283–292). Both methionines have an equal degree of similarity with the consensus sequence. However, the second methionine is thought to be the initiating methionine because the amino terminal sequence of the purified Oncostatin M (see above and Zarling, et al., *Proc. Natl. Acad. Sci. USA* (1986) 83:9739–9743) starts at the alanine next to this methionine.

The amino acid sequence of the Oncostatin M polypeptide deduced from the isolated cDNA clone shows that the protein has 228 amino acids with a molecular weight of 26,000 which is in close agreement with the approximate $M_r=28,000$ as determined by the polyacrylamide gel electrophoresis of the purified Oncostatin M (Zarling, et al., 1986 supra).

Earlier protein chemistry work (Zarling et al., 1986 supra) shownend that Oncostatin M is a glycoprotein. The cDNA clone sequence suggests two potential N-glycosylation sites (Hubbard and Ivatt, *Ann. Rev. Biochem.* (1981) 50:555–583) located at amino acids 76 and 193. The nucleotide-derived protein sequence shows that Oncostatin M is an extremely hydrophilic molecule with only a few weakly hydrophobic stretches of a few amino acids at the N-terminus and around amino acid −75.

The cDNA clone has a 384 bp untranslated 5' and a 1054 bp 3' untranslated region. However, the isolated clone lacked a polyA tail and polyadenylation recognition site.

D. Poly(A+) RNA in Different Cell Types

Figure 4:
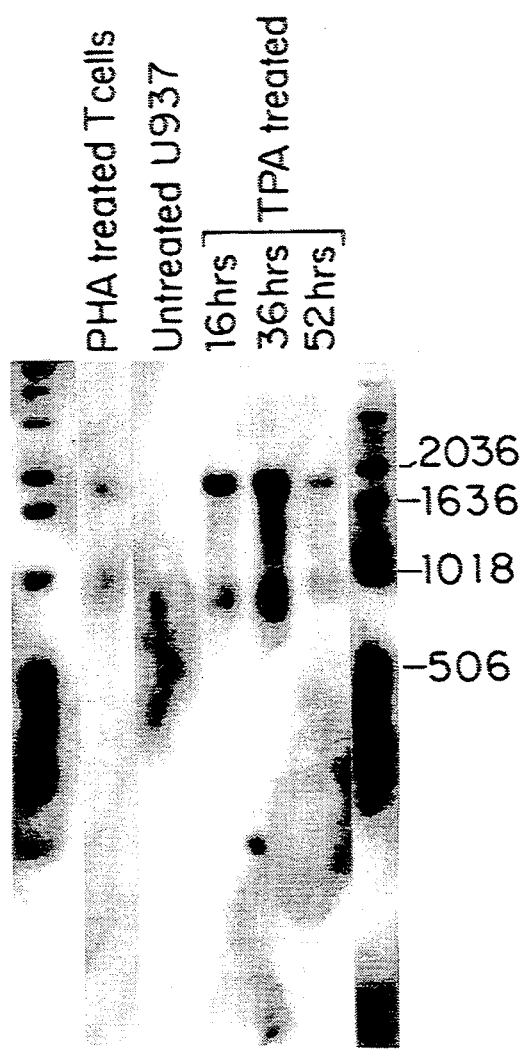
FIG. 4 is a photograph of Northern blot analysis of poly(A+) RNA in TPA treated and untreated U937 cells and PHA stimulated normal T-cells.

FIG. 4 shows a Northern blot analysis using a [$^{32}$P] labeled nick translated 2.1 Kb cDNA insert as a probe. Polyadenylated RNA isolated from U937 cells (histiocytic lymphoma cell line), which were either not treated with PMA or treated with the phorbol ester PMA for 16, 36 and 52 hrs, were run on a 1.5% denaturing formaldehyde agarose gel blotted on to hybond-N membranes and probed with the above probe. PMA-treated U937 cells showed two Oncostatin M-specific mRNA species with a size of approximately 2.1 Kb and 1 Kb. After 16 hrs of PMA treatment the Oncostatin M poly(A+) RNA was induced. The amount of poly(A+) RNA induced was further elevated after treatment for 36 hrs, but decreases after 52 hrs of treatment with PMA.

In addition, under less stringent binding conditions an additional 500 bp fragment in both treated and untreated U937 cells shows hybridized to the probe. Non-PMA treated U937 cells showed insignificant amount of Oncostatin M mRNA.

Oncostatin M mRNA bands were found in epithelium, liver and placenta, HeLa and IM9 cell lines. The mRNA was found in abundance in normal human placenta and in lesser amounts in liver and epithelium. The size of mRNA reacting with a nick-translated Oncostatin M cDNA clone in all these cases was about 1.5 kb. However, the size of the mRNA in these tissues differed from that found in PMA treated U937 cells.

Example 8

Oncostatin M Expressed in Recombinant Bacteria

A. Preparation of Cloning and Expression Plasmids
1. Plasmid pBM16/NDP. See co-pending U.S. application Ser. No. 115,139, filed Oct. 30, 1987 (Liu et al.), attorney docket number CT-1836.
2. Plasmid pBM11 allows cloning of a foreign gene downstream of the DNA sequences coding for the 33 N-terminal amino acids of the bacteriophage λ N-gene at a BamHI restriction site. Upon induction of the λ PL promoter by inactivation of the C1857 temperature-sensitive repressor at 42° C., the foreign gene product is expressed as the C-terminal part of a fusion protein in which the N-terminal sequence is that of the N-gene.
3. Plasmid pBM11M4 is derived from pBM11 and allows a foreign gene to be cloned at a BamHI restriction site directly after the initiating methionine of the N-gene.
4. Plasmid pBM11M3/PAD is derived from plasmid pBM11M4 and allows a foreign gene to be cloned at a HindIII, SmaI or BamHI downstream from a modified alkaline phosphatase signal sequence.
5. Plasmid pSMI,2/tac was developed by splicing the replication origin and beta-lactamase gene of pBR322 (Bolivar et al., *Gene* (1977) 2:95), the tac promoter and ribosomal binding sites of Cro gene (Roberts et al., *Proc. Natl. Acad. Sci. USA* (1979) 76:760–764) to the i-Z fused gene of pLG300 (Guarente et al, *Cell* (1980) 20:543–553).

B. Preparation of Recombinant Oncostatin M Genes
1. Construction of pSMI,2/tac-OncM.

In this construct, the entire coding sequence for the Oncostatin M gene is expressed as the C-terminal portion of a fusion protein having the first 21 amino acids of the λ cro protein at the N-terminus.

a. Preparation of pOncMVV2.

The 2.1 Kb Oncostatin M cDNA was excised from the λ phage recombinant, λ46 (see Example 7A) by EcoRI digestion. The insert was cloned into pEMBL18 (Dente et al., *Nucl. Acid Res.* (1983) 11:1645–1655) at the EcoRI site to produce clone pOncM46-15 vector with the Oncostatin M coding sequence opposed to the lac Z' sequence. The 5' noncoding sequence of Oncostatin M was removed by SalI and BglII double digestion of pOncM46-15 and replaced by a synthetic 80 bp SalI-BglII fragment to provide new BamHI and NcoI sites. The resulting clone was termed pOncMEV5. The sequence of the 80 bp fragment is as follows:

```
5' - TCGACGGATCCACCATGGCGGCGATCGGCAGCTGCTCG
3' - GCCTAGGTGGTACCGCCGCTAGCCGTCGACGAGC

AAAGAGTACCGCGTGCTCCTTGGCCAGCTCCAGAAGCAGACA - 3'
TTTCTCATGGCGCACGAGGAACCGGTCGAGGTCTTCGTCTGTCTAG - 5'
```

The coding sequence of Oncostatin M was excised from pOncMEV5 by XhoI and SalI double digestion as a 0.7 Kb fragment and cloned into the pUC8 vector at the SalI site. The clone pOncMVV2, containing the cDNA insert with the coding sequence opposed to the lac Z' sequence, was isolated. The 0.7 Kb NcoI-BamHI and the 0.7 Kb BamHI-BamHI fragment excised from clone pOncMVV2 were used to construct a λpL-based (pBM16/NDP/OncM) and a pSMI,2/tac-based (pSMI,2/tac-OncM) expression vector, respectively.

b. Preparation of pSMI,2/tac-OncM.

The DNA fragment encoding Oncostatin M was excised from pOncMVV2 by BamHI digestion and purified by gel electrophoresis. It was then cloned into expression vector, pSMI,2/tac, at the BamHI site. The DNA was used to transform *E. coli* RB791. The clone pOncME6 was isolated and confirmed to carry the predicted sequence.

2. Construction of pBM16/NDP/OncM
a. Preparation of modified Oncostatin M gene fragment.

Plasmid pOncMVV2 containing a modified Oncostatin M gene was digested with NcoI and BamHI and the 700 bp NcoI-BamHI Oncostatin M gene was gel purified. This fragment contained the NcoI overhang at the 5' end of the gene and the BamHI overhang at the 3' end of the gene.

b. Preparation of pBM16/NDP.

Plasmid pBM11/NDP/VGF (see copending U.S. application Ser. No. 115,139, filed Oct. 30, 1987 (Liu et al.), attorney docket number CT-1836) was digested with NcoI and BamHI which removes the synthetic gene TVV from the pBM16/DP plasmid fragment. The pBM16/NDP NcoI-BamHI 5.5 kb plasmid fragment was gel purified. The NcoI site in this fragment is positioned downstream of the nucleotide sequences coding for the first 32 amino acids of the N-gene and directly after the sequences coding for the acid labile dipeptide Asp-Pro.

c. Ligation and isolation of pBM16/NDP/OncM.

The 700 bp NcoI-BamHI fragment of the modified Oncostatin M gene and the NcoI-BamHI fragment of the plasmid pBM16/NDP were ligated together with T4 ligase and transformed into competent HB101 E. coli. The transformants were screened for correct construction by nucleotide sequencing using the Sanger-dideoxy technique. A correct colony was chosen and termed pBM16/NDP/OncM.

3. Construction of pBM11/PA/OncM a. Preparation of modified Oncostatin M gene fragment.

Plasmid pOncMVV2 containing a modified Oncostatin M gene was digested with NcoI and the 5' overhanging bases were removed by treatment with S1 nuclease leaving the fragment blunt-ended. The nuclease treatment removed the codons for the initiating methionine. The plasmid was further digested with BamHI and the 700 bp NcoI(blunt)-BamHI Oncostatin M gene fragment was gel purified. This fragment contained the NcoI blunt end at the 5' end of the gene and BamHI overhang at the 3' end of the gene.

b. Preparation of pBM11M3/PAD fragments.

Plasmid pBM11M3/PAD containing the nucleotide sequences coding for a modified alkaline phosphatase signal sequence was digested with HindIII which cuts directly downstream of the signal sequence. The overhanging ends were filled in and made blunt using Klenow fragment of DNA polymerase. The resulting DNA was further digested with PvuI and the 680 bp HindIII(blunt)-PvuI fragment was gel purified.

Plasmid pBM11M3/PAD was also digested with BamHI and PvuI and the 5 kb BamHI-PvuI fragment was gel purified.

c. Ligation and isolation of pBM11/PA/OncM.

The 700 bp NcoI(blunt)-BamHI Oncostatin M gene fragment, the 680 bp HindIII(blunt)-PvuI fragment of pBM11M3/PAD and the 5 kb BamHI-PvuI fragment of pBM11M3/PAD were ligated together using T4 ligase and transformed into competent HB101 E. coli. Correct construction was assayed by nucleotide sequencing using the Sanger-dideoxy technique. A correct colony was chosen and designated pBM11/PA/OncM.

C. Preparation of Recombinant Proteins

1. Recombinant Cell Culture:

a. Preparation of Oncostatin M Using pSMI,2/tac-OncM.

The E. coli strain, RB791 (thyA36, strA, LacI$^q$, L$_8$, λ$^+$, M$^+$) harboring pOncME6 was grown up to log phase and induced by isopropyl β-D-thiogalactoside at 37° C. for 4 hrs with shaking. The cells were harvested and analyzed for the presence of recombinant Oncostatin M.

b. Preparation of Oncostatin M using pBM16/NDP/OncM.

E. coli HB101 strain harboring the plasmid pBM16/NDP/OncM, which encodes the first 32 amino acids of the bacteriophase λ N-gene fused to an acid cleavable dipeptide (DP), and the synthetic OncM gene was grown at 30° C. At an OD600 of approximately 0.9 the temperature was raised to 42° C. which inactivates the temperature sensitive repressor inducing the PL promoter to allow transcription and translation of the NDP/OncM fusion gene. The fusion protein is characterized by having the 32 amino-terminal residues of the bacteriophage λ N-gene followed by the acid labile dipeptide Asp-Pro followed by the 228 amino acids of Oncostatin M including its N-terminal methionine.

c. Preparation of Oncostatin M Using pBMX.

An 82 bp fragment was synthesized chemically as shown below.

```
5' - CATGGCCATTGAAGGGCGCGCTGCGATCGGCAGCTGCTCGAAA
3' - CGGTAACTTCCCGCGCGACGCTAGCCGTCGACGAGCTTT

GAGTACCGCGTGCTCCTTGGCCAGCTCCAGAAGCAGACA - 3'
CTCATGGCGCACGAGGAACCGGTCGAGGTCTTCGTCTGTCTAG - 5'
```

The 82 bp fragment and truncated OncM cDNA (BglII-HindIII) isolated from pOncMVV2 were cloned into the pBM16/NDP/TVV vector prepared by NcoI and HindIII double digestion. The DNA was used to transform E. coli DH5α. The clone pBMX was isolated and confirmed to carry the predicted sequence. Since the coding sequence contains the -I-E-G-R-, a factor X recognition site, precisely fused to the N-terminal of mature OncM, the recombinant protein produced by pBMX should be cleaved at the R residue of -I-E-G-R- to generate mature OncM with the authentic N-terminal sequence following treatment of activated factor X. Similar procedures were used to prepare Oncostatin M using pBMX as to prepare Oncostatin M from pBM16/NDP/OncM.

2. Purification of Recombinant Oncostatin M

Recombinant OncM fusion proteins were purified from E. coli as follows: A cell pellet from a 500 ml culture of E. coli was suspended in 40 ml of PNE buffer (0.5M NaCl, 10 mM EDTA, 50 mM sodium phosphate), and lysed by sonication. Aggregated proteins were collected from the cell lysate by centrifugation. Aggregated proteins were sequentially extracted for 16 hrs each with 120 ml of 8M urea solutions buffered as follows: Solution 1) 20 mM Tris, pH 5; Solution 2) 20 mM Tris, pH 8; Solution 3) 50 mM Tris, pH 11. Most aggregated proteins were solubilized by Solutions 1 and 2, while recombinant Onco M remained insoluble until treatment with Solution 3.

3. Refolding of Recombinant Molecules

The Solution 3 extract was then dialyzed for 24 hrs against a refolding buffer (1M guanidine HCl, 1.2 mM oxidized glutathione, 0.2 mM reduced glutathionine, 20 mM Tris HCl, pH 8.0-9.0). Lowering the pH to <pH 8.0 resulted in a 100-fold reduction in yield of biologically active OncM. Following re-folding, proteins were dialyzed versus 1N acetic acid before testing in the GIA.

Example 9

Oncostatin M Expressed in Mammalian Cells

A. Preparation of Cloning and Expression Plasmids
1. Plasmid pSV2 Neo.

Plasmid pSV2 Neo is described in Southern et al., *J. of Mol. and Applied Genetics* (1982) 1:327–341.

2. Plasmid pH3M.

Plasmid pH3M (Aruffo et al., *Proc. Natl. Acad. Sci. USA* (1987) 84:3365–3369) was obtained from Dr. Alisandro Aruffo and Dr. Brian Seed. Briefly, the plasmid is constructed from pSV (Little et al., *Mol. Biol. Med.* (1983) 1:473–488) by inserting a synthetic transcription unit between the supressor tRNA gene and the SV40 origin. The transcription unit consists of a chimeric promoter composed of the human cytomegalovirus (CMV) AD169 immediate early enhancer fused to the HIV LTR −67 to +80 sequences. Immediately downstream from the LTR +80 sequence is a polylinker containing two BstXI sites. The BstXI are flanked by XhoI sites and XbaI sites. Downstream from the polylinker is the small t antigen splice and early region polyadenylation signals derived from pSV2 (Southern et al., *J. Mol. and Applied Genetics* (1982) 1:327–341). The pH3M plasmid originally contained cDNA sequences for a T-cell antigen cloned into the BstXI site of the polylinker. This cDNA was removed by digestion with XhoI. The plasmid was then purified by agarose slab gel electrophoresis and recircularized by ligating the complementary XhoI sequences.

3. Plasmid pSV2βTGF is described in Gentry et al., *Mol. Cell. Biol.* (1987) 7:3418–3427.

4. Plasmid pOncMVV2. See Example 8B1a.

5. Plasmid pSV2dhfr (Subramani et al., *Mol. Cell. Biol.* (1981) 1:854–864) contains the mouse dihydrofolate reductase (dhfr) gene under the control of the SV40 simian virus promoter.

6. Plasmid pSV2OncM contains the Oncostatin M gene under the control of the SV40 simian virus promoter (Subramani et al., *Mol. Cell. Biol.* (1981) 1:854–864). It was prepared as follows.

a. Preparation of a 700 bp HindIII-EcoRI (blunt) fragment of pOncMVV2.

Plasmid pOncMVV2, containing a modified Oncostatin M gene with NcoI site at 5′ end and BamHI site at the 3′ end, was cut at the EcoRI site in the polylinker region beyond the coding region at the 3′ end. The site was blunted by filling in with Klenow fragment of DNA polymerase I. HindIII was used to cut the fragment at the HindIII site located in the polylinker region beyond the initiating methionine at the 5′ end. The 700 bp HindIII-EcoRI (blunt ended) fragment was purified by separation on low melting temperature agarose gel.

b. Preparation of 4 kb pSV2 fragment lacking Neomycin resistance gene.

Plasmid pSV2Neo was cut with HpaI, filled in with Klenow fragment of DNA polymerase I to blunt end the fragment. The plasmid was digested with HindIII, and separated on low melting temperature agarose. The 4 kb fragment obtained had an SV40 early promoter, an intron and a polyadenylation signal.

c. Ligation and isolation of pSV2OncM.

The 700 bp HindIII-EcoRI blunt fragment of pOncMVV2 was ligated with 4 kb fragment lacking HindIII-HpaI fragment containing the Neo resistance gene. The resulting plasmid was termed as pSV2OncM. The 4–7 kb pSV2OncM contained the SV40 early promoter 5′ to the Oncostatin M gene, and an intron and polyadenylation signal 3′-proximal to the Oncostatin M gene.

B. Preparation of Recombinant Oncostatin M Genes
1. Construction of pSV2βOncM

The Oncostatin M cDNA sequence translates into a protein which has no strong hydrophobic domain which can serve as leader peptide and help the protein in being secreted out of the cells. Mammalian expression vectors were made with the thought that Oncostatin M genes may express a protein but may not be transported out of the cells because of the lack of secretory domain. To overcome this problem, a plasmid was made in which a monkey βTGF leader sequence was fused to the Oncostatin M coding region. This was accomplished in several steps.

a. Preparation of NaeI-EcoRI fragment of pSV2βTGF.

Plasmid pSV2βTGF was digested with EcoRI and NaeI. The NaeI site is 14 nucleotides upstream from the first amino acid of the βTGF precursor. This treatment removes the whole precursor and mature βTGF coding region. The digested fragment was isolated by gel separation.

b. Preparation of 2 kb EcoRI-BglII fragment of pSV2ncM.

pSV2OncM was disgested with EcoRI and BglII. The fragment was isolated by separation on an LMP agarose gel. The 2 kb fragment contained part of the pSV2 polyadenylation signal and a portion of the coding region of Oncostatin M, namely from the first amino acid of Oncostatin M up to the BglII site.

c. Preparation of Synthetic Oligonucleotides.

Synthetic oligonucleotides were obtained by using an oligonucleotide synthesizer. One oligonucleotide was a 77 mer and the second was an 81 mer nucleotide. The two oligonucleotides were annealed and used to fuse the DNA sequence encoding the last amino acid of the βTGF leader peptide and the DNA sequence encoding the first 21 amino acids of Oncostatin M.

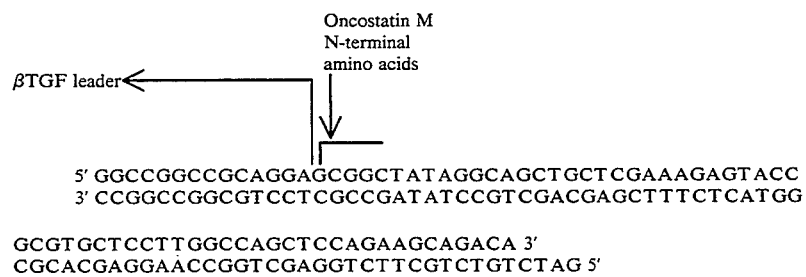

```
5' GGCCGGCCGCAGGAGCGGCT AT AGGCAGCT GCT CGAAAGAGT ACC
3' CCGGCCGGCGT CCT CGCCGAT AT CCGT CGACGAGCT TT CT CATGG

GCGT GCT CCTT GGCCAGCT CCAGAAGCAGACA 3'
  CGCACGAGGAACCGGT CGAGGT CTT CGT CT GT CT AG 5'
``` d. Ligation and isolation of pSV2βOncM.

A three-way ligation was carried out whereby the NaeI-EcoRI fragment of pSV2βTGF, the EcoRI-BglII fragment of pSV2OncM and the double-stranded synthetic oligonucleotide piece with BglII overhang at 5' end and NaeI site at 3' end were ligated. The resulting plasmid was termed pSV2βOncM. The plasmid has the DNA sequence encoding the monkey βTGF leader sequence fused to the DNA sequence encoding Oncostatin M. The βOncM coding regions were sequenced and were shown to be fused in the desired orientation, i.e., the last amino acid of the leader sequence of βTGF was fused to the first alanine of mature Oncostatin M.

C. Preparation of Recombinant Oncostatin M

1. Transient Expression in COS cells a. Subcloning of Oncostatin M Gene: Preparation of pH3M/βOncM.

The construction of pH3M/βOncM plasmid was done in three steps. The first step was to prepare a cloning site in the expression vector pH3M. This was accomplished by cutting at the XhoI site in the polylinker and then blunting the ends with the Klenow fragment of DNA polymerase I. The linearized plasmid was then cut at the HindIII site 22 base pairs 5' to the XhoI site and purified by agarose gel electrophoresis. The second step was to isolate the fragment containing the βTGF leader sequence fused to the Oncostatin M coding sequence from plasmid pSV2/βOncM, described above. This was done by cutting at the BamHI site in the polylinker just 3' to the gene, blunting the ends with the Klenow fragment of DNA polymerase I, then cutting at the HindIII site at the 5' end of the gene in the polylinker. The fragment was purified by agarose gel elecrophoresis. The final step in the construction was the insertion of this HindIII-BamHI (blunt) fragment into the HindIII-XhoI (blunt) site of the vector.

b. Transfection of pH3M/βOncM into COS cells.

COS cells (Gluzman, Cell (1981) 23:175–182) were maintained in Dulbecco's Modified Eagle's Medium (DMEM) with 10% fetal bovine serum, 100 μl/ml streptomycin, and 100 units/ml penicillin at 37° C. in a humidified atmosphere containing 6% $CO_2$.

For transfection, the COS cells were plated into 60 or 100 mm tissue culture dishes at a density to achieve 50% confluence and cultured as described for 16–20 hours. Immediately prior to transfection the medium was replaced with DMEM containing 10% heat inactivated Nuserum (Collaborative Research) and 100 μM chloroquine diphosphate. A transfection cocktail containing 167 μg/ml DNA and 10 mg/ml DEAE dextran in PBS was then added to the cell culture medium to give a final DNA concentration of 10 μg/ml, and incubated at 37° C. After 2–3 hours the transfection medium was removed and replaced with PBS containing 10% DMSO for 2 min. at room temperature. Cells were then rinsed twice in DMEM with 10% FBS at 37° C. After 16–20 hours the medium was changed to serum free DMEM. The cells were then incubated for 48 hours at 37° C. The medium was collected and clarified by centrifugation to remove cell debris then tested, without further purification, in the growth inhibition assay (see Example 1B).

2. In CHO Cells a. Preparation of pSV2OncM/dhfr and pSV2βOncM/dhfr.

pSV2βOncM/dhfr, which contains the human Oncostatin M gene and the βTGF leader sequence fused to the Oncostatin M gene, the mouse dhfr gene as well as the SV40 promoter and intervening SV40 sequences, and pSV2OncM/dhfr, which lacks the βTGF leader sequence, were constructed as follows. In the first step, a NdeI-EcoRI (blunt) fragment of pSV2OncM or pSV2βOncM was obtained. The 2.3–2.6 kb fragments were gel purified. In the next step, plasmid pSV2dhfr was digested with NdeI-PvuII and a 4 kb fragment was gel purified. In the final step, pSV2dhfr cut with PvuII-NdeI was ligated to either a NdeI-EcoRI blunted pSV2OncM or pSV2βOncM fragment.

b. Transfection of dhrf⁻ CHO cells by pSV2βOncM/dhfr or pSV2βOncM/dhfr.

Plasmid pSV2OncM/dhfr or pSV2βOncM/dhfr was transfected by calcium phosphate precipitation into CHO cells. Cells are adapted to grow in the presence of increasing concentrations of methotrexate resulting in amplification of the gene (see Gasser et al., *J. Biol. Chem.* (1986) 261:6938–6946), and are then assayed for Oncostatin M expression by measuring inhibition of replication of A375 cells.

c. Subcloning of Oncostatin M Gene: Preparation of plasmid pSVDR/βOncM.

This construct, which was shown to transiently express Oncostatin M in COS cells as described above, is used to transform dhfr-deficient Chinese hamster ovary cells (Urlaub et al., *Proc. Natl. Acad. Sci. USA* (1980) 77:4216–4220).

Plasmid pSVDR/βOncM was constructed by inserting the β-Oncostatin M transcriptional unit from plasmid pH3M/βOncM (see Example 9A2), into plasmid pSV2/dhfr. The plasmid was constructed in three steps. First, plasmid pH3M/βOncM was cut at the NruI site just 5' to the CMV enhancer region and at the BamHI site 3' to the polyadenylation and transcription termination signal for the Oncostatin M gene. The resulting fragment was purified by agarose gel electrophoresis. In the second step, plasmid pSV2/dhfr was cut at the BamHI site 3' to the polyadenylation and transcription termination signal for the mouse dihydrofolate reductase gene. The third step was to insert the NruI-BamHI Oncostatin M gene containing fragment into the BamHI site of the vector plasmid pSV2/dhfr by first joining the DNA fragments at their BamHI ends then blunting the remaining BamHI overhang with Klenow. The final blunt end ligation yielded the plasmid pSVDR/βOncM.

Example 10

Oncostatin M Expressed in Insect Cells

A. Description of Cloning and Expression Vectors

1. Plasmid pAc610 (Smith et al., *Mol. Cell. Biol.* (1983) 12:2156–2165), allows expression of a foreign gene in insect cells.

B. Preparation of Recombinant Oncostatin M Genes

1. Preparation of plasmid pAc/OncM: Transfection of this plasmid into insect cells, *Spodoptera frugiperda* (sfg) allows Oncostatin M to be expressed under the control of the baculovirus polyhedrin gene regulators.

a. Preparation of BamHI digested pAc610:
Plasmid pAc610 was digested with BamHI.

b. Preparation of BamHI-BamHI fragment of the Oncostain M gene:
pOncMVV2 was digested with BamHI and the 700 bp fragment was gel purified.

c. Ligation and isolation of pAc/OncM:
The BamHI digested pAc610 and the 700 bp BamHI fragment of pOncMVV2 containing the Oncostatin M gene were ligated together using DNA ligase and the transformants were screened by restriction analysis. A correct construct was isolated and termed as pAc-/OncM.

C. Preparation of Recombinant Oncostatin M

1. Transfection of Sf9 cells with pAc/OncM:

Plasmid pAc/OncM was co-transfected with AcNPV wild-type baculovirus DNA into Sf9 insect cells (Spodoptera frugiperda). The transfectants were screened for occlusion negative phenotype in plaque assays. One occlusion negative plaque was isolated and after five rounds of successive plaque purification, a high titer recombinant virus stock was prepared. Supernatants obtained from the infected cells 48 hours after transfection were assayed for Oncostatin M activity.

Example 11

Biological Activity of Oncostatin M

A. Growth Inhibitory Activity

Biological activity of recombinant Oncostatin M was assessed by a growth inhibitory assay. Briefly, aliquots of extracts from transformed cells or medium from cell cultures were lyophilized with 20 μg bovine serum albumin as a carrier protein, resuspended in DMEM containing 10% fetal calf serum, and diluted serially before addition to 96-well cultures containing A375 cells ($3.5 \times 10^3$ cells/well). Cells were grown at 37° C. for 72 hrs, and analyzed for relative proliferation by staining with crystal violet as described by Sugarman et al., Cancer Research (1987) 47:780-786. The absorbance of bound dye at 590 nm was measured on a microtiter plate reader (Genetic Systems, Seattle, Wash). Recombinant Oncostatin M was prepared using the following expression systems: E. coli, COS cells, CHO and insect cells (sf9). The data are summarized in the following table.

inhibits the growth of A375 cells by 50%). No activity was detected in the medium of COS cells transfected with plasmid pH3M alone or plasmid pH3M containing just the Oncostatin M sequences.

Example 12

Physicochemical Characterization of Recombinant Oncostain M Expressed in Bacteria

A. SDS-PAGE

Cultures (50 ml) were grown and induced as described. Cultures were pelleted and the cell pellets were solubilized in 6M guanidine HCl. Insoluble proteins were not removed at this point. Samples for SDS-PAGE analysis were dialyzed directly against 1N acetic acid without refolding.

Aliquots consisting of approximately 6 μg of total bacterial protein were analyzed by SDS-PAGE on 10–20% gradient gels (5% stacking gel). Gels were stained with Coomassie Brilliant Blue, destained and dried. The apparent molecular weight $M_r$ of the NDP-OncM fusion protein was estimated to be 32,000 by comparison of its mobility with that of standard proteins.

It is evident from the above results, that a novel polypeptide and polypeptide fragments are provided, which can be used for modulating cellular growth. The compound is found to have varying activity depending upon the nature of the cell line involved, so that it may be used by itself or in conjunction with other compounds in modulating cellular growth. The subject polypeptides therefore add an additional polypeptide which may be used with mixtures of cells, both in vivo and in vitro, to selectively reduce or enhance cellular proliferation of a particular type of cell.

TABLE 8

| | Growth Inhibitory Activity of Recombinant Oncostatin M | | | | |
|---|---|---|---|---|---|
| Plasmid | Expression Level % Total Protein[1] | Units/ml[2] | Highest purity[3] | Sp. Act[4] | Immunoreactivity[5] |
| E. coli | | | | | |
| pBM16/NDP/OncM | ~20 | ND[6] | >80% | 7 | + |
| pSM1,2/tac/OncM | ~10 | ND | ND | ND | ND |
| pBM11/PA/OncM | ~5 | ND | ND | ND | + |
| pBMX | ~5 | ND | ~50% | 1 | + |
| COS cells pH3M/βOncM | <1 | 56,000 | ND | >10,000 | + |
| CHO cells pSV2βOncM/dhfr | ND | 10,000[7] | ND | ND | ND |
| Insect cells (sf9) pAc/OncM | ND | 1,800 | ND | ND | ND |

[1]Estimated from stained SDS PAGE gels of total protein.
[2]Growth inhibitory activity (GIA) units/ml.
[3]Preparation with highest purity.
[4]GIA units/ug protein. Fusion proteins produced in E. coli were purified and refolded before testing.
[5]Immunoreactivity in Western blots using a rabbit antiserum generated against a synthetic peptide corresponding to amino acid 6–19 of Oncostatin M. "+" indicates that the recombinant peptide is immunoreactive (non-quantitative).
[6]ND = Not done.
[7]Without amplification with methotrexate.

The data provide formal proof that the growth inhibitory activity ascribed to purified preparations of Onco M was in fact due to the Onco M protein. The data also show that bioactive Onco M can be produced in both prokaryotic and eukaryotic systems.

Medium from COS cells transfected with plasmid pH3M/βOncM was tested further for growth inhibitory activity as compared to COS cells transfected with plasmid pH3M alone, or plasmid pH3M containing Oncostatin M sequences without the fused βTGF leader sequence. With pH3M/βOncM, Oncostatin M activity of approximately 18,000 units/ml was detected (one unit is the amount of Oncostatin M added that It is also evident from the above results, that by using combinations of various growth regulatory materials, particularly Oncostatin M in conjunction with at least one other growth factor, such as transforming growth factors, γ-interferons or tumor necrosis factor, or active analogs or fragments thereof, substantially reduced dosages of the individual compositions may be employed, while still retaining growth modulating effect since the combination of factors can act in synergy. In particular, where dosages of Oncostatin M, TGF-β, γ-interferon, or tumor necrosis factor are unable to completely inhibit inhibition when used alone, Oncostatin M and at least one other growth regulatory factor may be combined at concentrations less than that required to give inhibition if their effects were added, to achieve substantially more inhibition of proliferation. The compositions can be used in the regulation of cell proliferation both in vivo and in vitro, such as in culture, leukophoresis, for prophylactic and therapeutic purposes in vivo, and the like.

In particular, the factors having Oncostatin M-like biological activity can be used to treat cells for autologous bone marrow transplants. Use of the factor inhibits the growth of tumor cells in the marrow and may stimulate colony cell formation. Oncostatin M may also be used to stimulate growth of epithelial cells thereby promoting wound healing. In addition, Oncostatin M and fragments thereof can be used as immunogens to induce antibody formation. The induced antibodies find use to titer Oncostatin M present in a bodily fluid or to modulate the activity of the factor by binding to it. Further, the antibodies together with purified Oncostatin M or fragments thereof serve as components of diagnostic kits in conjunction with other reagents, particularly antibodies, to detect and quantitate Oncostatin M.

Probes comprising sequences complementary to Oncostatin M mRNA can be used to determine the presence and amount of Oncostatin M mRNA in a sample, which in addition may be used to detect the presence of cancer cells. Cell surface receptors which bind Oncostatin M and related peptides may be used to predict sensitivity of the cell to Oncostatin M and like materials, as well as a means to screen for other peptides which have Oncostatin M-like biological activity.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following organisms have been deposited with In Vitro International, 611 P Hammonds Ferry Road, Linthicum, Md., 21090: *E. coli* HB101 containing plasmid pBM11/NDP/OncM, Accession No. IVI-10157, deposited Jan. 14, 1988.

Although the foregoing invention has been described in some detail by way of illustration and example for purposes of clarity of understanding, it will be obvious that certain changes and modifications may be practiced within the scope of the appended claims.

What is claimed is:

1. A neoplastic cell proliferation inhibiting composition comprising a cell proliferation inhibiting amount of oncostatin M in a physiologically acceptable carrier.

2. A neoplastic cell proliferation inhibiting composition according to claim 1, further comprising a tumor necrosis factor-α.

3. A substantially pure polypeptide having an amino acid sequence comprising:

```
                        10                              20                              30
A—A—I—G—S—C—S—K—E—Y—R—V—L—L—G—Q—L—Q—K—Q—T—D—L—M—Q—D—T—S—R—L—

40                              50                              60
L—D—P—Y—I—R—I—Q—G—L—D—V—P—K—L—R—E—H—C—R—E—R—P—G—A—F—P—S—E—E—

70                              80                              90
T—L—R—G—L—G—R—R—G—F—L—Q—T—L—N—A—T—L—G—C—V—L—H—R—L—A—D—L—E—Q—

100                             110                             120
R—L—P—K—A—Q—D—L—E—R—S—G—L—N—I—E—D—L—E—K—L—Q—M—A—R—P—N—I—L—G—

130                             140                             150
L—R—N—N—I—Y—C—M—A—Q—L—L—D—N—S—D—T—A—E—P—T—K—A—G—R—G—A—S—Q—P—

160                             170                             180
P—T—P—T—P—A—S—D—A—F—Q—R—K—L—E—G—C—R—F—L—H—G—Y—H—R—F—M—H—S—V—

190                             200                             210
G—R—V—F—S—K—W—G—E—S—P—N—R—S—R—R—H—S—P—H—Q—A—L—R—K—G—V—R—R—T—

220                     227
R—P—S—R—K—G—K—R—L—M—T—R—G—Q—L—P—R
``` having biological activity of oncostatin M.

4. A polypeptide according to claim 3, wherein the specific activity of said polypeptide is from about 10 to about 100 units growth inhibitory activity/ng protein.

* * * * *